United States Patent
Bartnik et al.

(10) Patent No.: US 6,180,334 B1
(45) Date of Patent: Jan. 30, 2001

(54) ARTIFICIAL RECOMBINANT SUBSTRATE (RAGG 1) AND NATIVE AGGRECAN TO DETERMINE THE PROTEOLYTIC ACTIVITY OF 'AGGRECANASE' IN CELL CULTURE SYSTEMS

(75) Inventors: Eckart Bartnik, Wiesbaden-Delkenheim; Bernd Eidenmueller, Frankfurt; Frank Buettner, Ludwigshafen, all of (DE); Bruce Caterson; Clare Hughes, both of Wales (GB)

(73) Assignee: Aventis Pharma Deutschland GmbH, Frankfurt am Main (DE)

( * ) Notice: Under 35 U.S.C. 154(b), the term of this patent shall be extended for 0 days.

(21) Appl. No.: 09/176,228

(22) Filed: Oct. 21, 1998

Related U.S. Application Data

(62) Division of application No. 08/784,512, filed on Jan. 17, 1997, now Pat. No. 5,872,209.

(30) Foreign Application Priority Data

Jan. 18, 1996 (EP) ................................................ 96100682

(51) Int. Cl.[7] .................................................... C12Q 1/00
(52) U.S. Cl. ................................. 435/4; 435/7.1; 435/7.4; 435/7.21; 435/252.3; 435/254.11; 435/320.1; 435/325; 435/455; 435/471; 536/23.1; 536/23.5
(58) Field of Search .................................. 435/4, 7.4, 7.1, 435/7.21, 23, 24, 252.3, 254.11, 325, 320.1, 455, 471; 536/22.1, 23.1

(56) References Cited

U.S. PATENT DOCUMENTS 5,872,209 * 2/1999 Bartnik et al. .................. 530/324

FOREIGN PATENT DOCUMENTS

WO 93/22429   11/1993  (WO) .

OTHER PUBLICATIONS

Prickett, Kathryn S. et al., "A Calcium–Dependent Antibody for Identification and Purification of Recombinant Proteins," *BioTechniques* vol. 7 No. 6, pp. 580–589 (1989).
Ilic, Mirna Z. et al., "The N–Terminal Sequence of the Large Proteoglycan of Articular Cartilage," *Biochem. Int'l.*, vol. 21, No. 5, pp. 977–986 (Aug. 1990).
Laemmli, U.K. "Cleavage of Structural Proteins during the Assembly of the Head of Bacteriophage T4," *Nature*, vol. 227, pp. 680–685 (Aug. 1970).
Aydelotte, Margaret B. et al., "Differences Between Sub-Populations of Cultured Bovine Articularchondrocytes. I. Morphology and Cartilage Matrix Production," *Conn. Tissue Res.*, vol. 18, pp. 205–222 (1988).
Arruffo, Alejandro et al., "CD44 is the Principal Cell Surface Receptor for Hyaluronate," *Cell*, vol. 61 pp. 1303–1313 (Jun. 1990).
Adams, Mark E. et al., "Extraction and Isolation of mRNA from Adult Articular Cartilage," *Anal. Biochem.*, vol. 202, pp. 89–95 (1992).
Lohmander, L. Stephan et al., "The Structure of Aggrecan Fragments in Human Synovial Fluid," *Arth. Rheum.*, vol. 36, No. 9, pp. 1214–1222 (Sep. 1993).
Morales, Teresa I. et al., "The Interaction between Retinoic Acid and the Transforming Growth Factors–β in Calf Articular Cartilage Organ Cultures", *Arch. Biochem. Biophys.*, vol 293, No. 1, pp. 79–84 (Feb. 1992).
Fosang, Amanda J. et al., "Effect of Interleukin–1 and Insulin Like Growth Factor–1 on the Release of Proteoglycan Components and Hyaluronan from Pig Articular Cartilage in Explant Culture," *Matrix*, vol. 11, pp. 17–24 (1991).
Tyler, Jenny A. "Chondrocyte–mediated depletion of articular cartilage proteoglycans in vitro," *Biochem. J.*, vol. 225, pp. 493–507 (1985).
Hughes, Clare E. et al., "Monoclonal antibodies that specifically recognize neoepitope sequences generated by 'aggrecanase' and matrix metalloproteinase cleavage of aggrecan: application to catabolism in situ and in vitro," *Biochem J.*, vol. 305, pp. 799–807 (1995).
Loulakis, Pat et al., "N–Terminal sequence of proteoglycan fragments isolated from medium of interleukin–1–treated articular–cartilage cultures," *Biochem. J.*, vol. 284, pp. 589–593 (1992).
Sandy, John D. et al., "Degradation of Proteoglycan in Articular Cartilage," *Biochim. Biophys. Acta*, vol. 543, pp. 536–544 (1978).
Hughes, Clare E. et al., "Monoclonal Antibodies Recognizing Protease–generated Neoepitopes from Cartilage Proteoglycan Degradation," *J. Biol. Chem*, vol. 267, No. 23, pp. 16011–16014 (1992).
Lark, Michael W. et al., "Cell–mediated Catabolism of Aggrecan," *J. Biol. Chem.*, vol. 270, No. 6, pp. 2550–2556 (Feb. 1995).
Doege, Kurt J. et al., "Complete Coding Sequence and Deduced Primary Structure of the Human Cartilage Large Aggregating Proteoglycan, Aggrecan," *J. Biol. Chem.*, vol. 266, No. 2, pp. 894–902 (1991).

(List continued on next page.)

Primary Examiner—Einar Stole
(74) Attorney, Agent, or Firm—Foley & Lardner

(57) ABSTRACT

The invention relates to novel recombinant substrates for aggrecanase. In one embodiment, this substrate comprises the signal sequence of CD5, the FLAG-epitope for M1 monoclonal antibody detection, the interglobular domain of human aggrecan, the hinge region of human IgG1, the CH2 region of human IgG1 and the CH3 region of human IgG1. DNA sequences encoding the recombinant substrate are also provided, as are vectors and host cells containing said DNA. Various methods are provided for: monitoring aggrecanase activity, detecting new enzymatic cleavage sites, purifying aggrecanase chromatographically, and cloning the aggrecanase cDNA, screening for aggrecanase inhibitors; and for monitoring the onset or progression of osteoarthritis. A diagnostic aid containing the recombinant substrate is also provided.

24 Claims, 10 Drawing Sheets

OTHER PUBLICATIONS

Ilic, Mirna Z. et al., "Mechanism of Catabolism of Aggrecan by Articular Cartilage," *Arch. Biochem. Biophys.*, vol. 294, No. 1, pp. 115–122 (Apr. 1992).

Fosang, Amanda J. et al., "Neutrophil collagenase (MMP–8) cleaves at the aggrecanase site $E^{373}$–$A^{374}$ in the interglobular domain of cartilage aggrecan," *Biochem. J.*, vol. 304 pp. 347–351 (1994).

Fosang, Amanda J. et al., "The Interglobular Domain of Cartilage Aggrecan is Cleaved by PUMP, Gelatinases, and Cathepsin B*," *J. Biol. Chem.*, vol. 267, No. 27, pp. 19470–19474 (Sep. 1992).

Fosang, Amanda J. et al., "Cleavage of Cartilage Proteoglycan between G1 and G2 Domains by Stromelysins*," *J. Biol. Chem.*, vol. 266, No. 24, pp. 15579–15582 (Aug. 1991).

Flannery, Carl R. et al., "Identification of a Stromelysin Cleavage Site within the Interglobular Domain of Human Aggrecan," *J. Biol. Chem.*, vol. 267, No. 2, pp. 1008–1014 (Jan. 1992).

Sandy, John D. et al., "Catabolism of Aggrecan in Cartilage Explants," *J. Biol. Chem.*, vol. 266, No. 14, pp. 8683–8685 (May 1991).

Dudhia, Jayesh et al., "Age–related changes in the content of the C–terminal region of aggrecan in human articular cartilage," *Biochem. J.*, vol. 313, pp. 933–940 (1996).

Lark, Michael W. et al., "Quantification of a matrix metalloproteinase–generated aggrecan G1 fragment using monospecific anti–peptide serum," *Biochem. J.*, vol. 307, pp. 245–252 (1995).

Fosang, Amanda J. et al., "Fibroblast and neutrophil collagenases cleave at two sites in the cartilage aggrecan interglobular domain," *Biochem. J.*, vol. 295 pp. 273–276 (1993).

Burrows, G.G. et al., "Expression, Purification and Biochemical Characterization of Recombinant Aggrecan G1, G2 and G3 Domains," *Abstracts Presented at The American Society for Cellular Biology Thirty–Third Annual Meeting*, p. 63a, Abstract No. 366, (Dec. 1993).

Sandy, John D. et al., "The Structure of Aggrecan Fragments in Human Synovial Fluid," *J. Clin. Invest.*, vol. 89, pp. 1512–1516 (May 1992).

* cited by examiner

Fig. 1 Structure of rAGG-1

EXPRESSION OF rAGG-1 IN COS CELLS

DETECTION WITH MI-MoAb

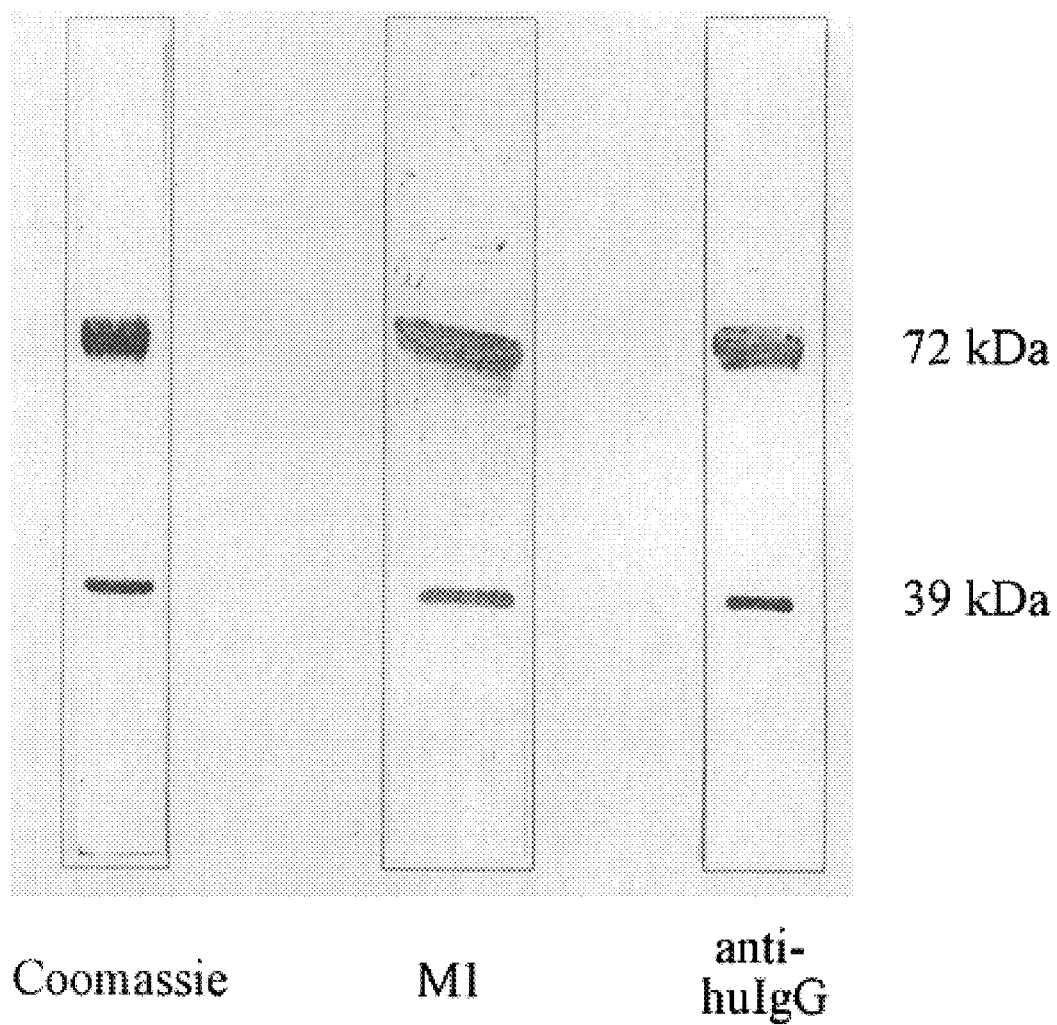

Screening Assay for "aggrecanase" activity rat chondrosarcoma cells

FIG. 6A

Amino Acid Sequence of rAGG-1 (SEQ ID NO: 3)

```
Met Pro Met Gly Ser Leu Gln Pro Leu Ala Thr Leu Tyr Leu Leu Gly
1               5                   10                  15

Met Leu Val Ala Ser Val Leu Ala Asp Tyr Lys Asp Asp Asp Asp Lys
                20                  25              30

Thr Gly Glu Asp Phe Val Asp Ile Pro Glu Asn Phe Phe Gly Val Gly
        35              40                  45

Gly Glu Glu Asp Ile Thr Val Gln Thr Val Thr Trp Pro Asp Met Glu
    50              55                      60

Leu Pro Leu Pro Arg Asn Ile Thr Glu Gly Ala Arg Gly Ser Val
65                  70              75                      80

Ile Leu Thr Val Lys Pro Ile Phe Glu Val Ser Pro Ser Pro Leu Glu
                85              90                  95

Pro Glu Glu Pro Phe Thr Phe Ala Pro Glu Ile Gly Ala Thr Ala Phe
            100             105                 110

Ala Glu Val Glu Asn Glu Thr Gly Glu Ala Thr Arg Pro Trp Gly Phe
        115                 120                 125

Pro Thr Pro Gly Leu Gly Pro Ala Thr Ala Phe Thr Ser Glu Asp Leu
    130             135                     140

Val Val Gln Val Thr Ala Val Pro Gly Gln Pro His Leu Pro Gly Gly
145                 150                 155                 160

Gly Asp Pro Glu Glu Pro Lys Ser Cys Asp Lys Thr His Thr Cys Pro
                165                 170                 175

Pro Cys Pro Ala Pro Glu Leu Leu Gly Gly Pro Ser Val Phe Leu Phe
            180                 185                 190

Pro Pro Lys Pro Lys Asp Thr Leu Met Ile Ser Arg Thr Pro Glu Val
        195                 200                 205

Thr Cys Val Val Val Asp Val Ser His Glu Asp Pro Glu Val Lys Phe
    210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Arg Glu Pro Gln Val Tyr Thr Leu Pro Pro Ser Arg
    290                 295                 300

Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335
```

FIG. 6B

Glu Asn Asn Tyr Lys Thr Thr Pro Pro Val Leu Asp Ser Asp Gly Ser
        340             345                 350

Phe Phe Leu Tyr Ser Lys Leu Thr Val Asp Lys Ser Arg Trp Gln Gln
        355             360                 365

Gly Asn Val Phe Ser Cys Ser Val Met His Glu Ala Leu His Asn His
    370             375                 380

Tyr Thr Gln Lys Ser Leu Ser Leu Ser Pro Gly Lys
385             390                 395

FIG. 7A

Sequence of pCDM8-rAGG-1 (prAGG-1IGG) (SEQ ID NO: 4)

| | | | | | |
|---|---|---|---|---|---|
| GGCGTAATCT | GCTGCTTGCA | AACAAAAAAA | CCACCGCTAC | CAGCGGTGGT | TTGTTTGCCG | 60 |
| GATCAAGAGC | TACCAACTCT | TTTTCCGAAG | GTAACTGGCT | TCAGCAGAGC | GCAGATACCA | 120 |
| AATACTGTCC | TTCTAGTGTA | GCCGTAGTTA | GGCCACCACT | TCAAGAACTC | TGTAGCACCG | 180 |
| CCTACATACC | TCGCTCTGCT | AATCCTGTTA | CCAGTGGCTG | CTGCCAGTGG | CGATAAGTCG | 240 |
| TGTCTTACCG | GGTTGGACTC | AAGACGATAG | TTACCGGATA | AGGCGCAGCG | GTCGGGCTGA | 300 |
| ACGGGGGGTT | CGTGCACACA | GCCCAGCTTG | GAGCGAACGA | CCTACACCGA | ACTGAGATAC | 360 |
| CTACAGCGTG | AGCATTGAGA | AAGCGCCACG | CTTCCCGAAG | GGAGAAAGGC | GGACAGGTAT | 420 |
| CCGGTAAGCG | GCAGGGTCGG | AACAGGAGAG | CGCACGAGGG | AGCTTCCAGG | GGGAAACGCC | 480 |
| TGGTATCTTT | ATAGTCCTGT | CGGGTTTCGC | CACCTCTGAC | TTGAGCGTCG | ATTTTTGTGA | 540 |
| TGCTCGTCAG | GGGGGCGGAG | CCTATGGAAA | AACGCCAGCA | ACGCAAGCTA | GCTTCTAGCT | 600 |
| AGAAATTGTA | AACGTTAATA | TTTTGTTAAA | ATTCGCGTTA | AATTTTTGTT | AAATCAGCTC | 660 |
| ATTTTTTAAC | CAATAGGCCG | AAATCGGCAA | AATCCCTTAT | AAATCAAAAG | AATAGCCCGA | 720 |
| GATAGGGTTG | AGTGTTGTTC | CAGTTTGGAA | CAAGAGTCCA | CTATTAAAGA | ACGTGGACTC | 780 |
| CAACGTCAAA | GGGCGAAAAA | CCGTCTATCA | GGGCGATGGC | CGCCCACTAC | GTGAACCATC | 840 |
| ACCCAAATCA | AGTTTTTTGG | GGTCGAGGTG | CCGTAAAGCA | CTAAATCGGA | ACCCTAAAGG | 900 |
| GAGCCCCCGA | TTTAGAGCTT | GACGGGGAAA | GCCGGCGAAC | GTGGCGAGAA | AGGAAGGGAA | 960 |
| GAAAGCGAAA | GGAGCGGGCG | CTAGGGCGCT | GGCAAGTGTA | GCGGTCACGC | TGCGCGTAAC | 1020 |
| CACCACACCC | GCCGCGCTTA | ATGCGCCGCT | ACAGGGCGCG | TACTATGGTT | GCTTTGACGA | 1080 |
| GCACGTATAA | CGTGCTTTCC | TCGTTGGAAT | CAGAGCGGGA | GCTAAACAGG | AGGCCGATTA | 1140 |
| AAGGGATTTT | AGACAGGAAC | GGTACGCCAG | CTGGACCGCG | GTCTTTCTCA | ACGTAACACT | 1200 |
| TTACAGCGGC | GCGTCATTTG | ATATGATGCG | CCCCGCTTCC | CGATAAGGGA | GCAGGCCAGT | 1260 |
| AAAAGCATTA | CCCGTGGTGG | GGTTCCCGAG | CGGCCAAAGG | GAGCAGACTC | TAAATCTGCC | 1320 |
| GTCATCGACT | TCGAAGGTTC | GAATCCTTCC | CCCACCACCA | TCACTTTCAA | AAGTCCGAAA | 1380 |
| GCTGCTCCCT | GCTTGTGTGT | TGGAGGTCGC | TGAGTAGTGC | GCGAGTAAAA | TTTAAGCTAC | 1440 |
| AACAAGGCAA | GGCTTGACCG | ACAATTGCAT | GAAGAATCTG | CTTAGGGTTA | GGCGTTTTGC | 1500 |
| GCTGCTTCGC | GATGTACGGG | CCAGATATAC | GCGTTGACAT | TGATTATTGA | CTAGTTATTA | 1560 |
| ATAGTAATCA | ATTACGGGGT | CATTAGTTCA | TAGCCCATAT | ATGGAGTTCC | GCGTTACATA | 1620 |
| ACTTACGGTA | AATGGCCCGC | CTGGCTGACC | GCCCAACGAC | CCCCGCCCAT | TGACGTCAAT | 1680 |
| AATGACGTAT | GTTCCCATAG | TAACGCCAAT | AGGGACTTTC | CATTGACGTC | AATGGGTGGA | 1740 |
| CTATTTACGG | TAAACTGCCC | ACTTGGCAGT | ACATCAAGTG | TATCATATGC | CAAGTACGCC | 1800 |

FIG. 7B

```
CCCTATTGAC GTCAATGACG GTAAATGGCC CGCCTGGCAT TATGCCCAGT ACATGACCTT    1860
ATGGGACTTT CCTACTTGGC AGTACATCTA CGTATTAGTC ATCGCTATTA CCATGGTGAT    1920
GCGGTTTTGG CAGTACATCA ATGGGCGTGG ATAGCGGTTT GACTCACGGG GATTTCCAAG    1980
TCTCCACCCC ATTGACGTCA ATGGGAGTTT GTTTTGGCAC CAAAATCAAC GGGACTTTCC    2040
AAAATGTCGT AACAACTCCG CCCCATTGAC GCAAATGGGC GGAATTCCTG GCGGGACTG    2100
GGGAGTGGCG AGCCCTCAGA TGCTGCATAT AAGCAGCTGC TTTTTGCCTG TACTGGGTCT    2160
CTCTGGTTAG ACCAGATCTG AGCCTGGGAG CTCTCTGGCT AACTAGAGAA CCCACTGCTT    2220
AAGCCTCAAT AAAGCTTCTA GAGATCCCTC GACCTCGAGA TCCATTGTGC TCTAAAGGAG    2280
ATACCCGGCC AGACACCCTC ACCTGCGGTG CCCAGCTGCC CAGGCTGAGG CAAGAGAAGG    2340
CCAGAAACCA TGCCCATGGG GTCTCTGCAA CCGCTGGCCA CCTTGTACCT GCTGGGGATG    2400
CTGGTCGCTT CCGTGCTAGC CGACTACAAG GACGACGATG ACAAGACAGG TGAAGACTTT    2460
GTGGACATCC AGAAAACTT CTTTGGAGTG GGGGGTGAGG AGGACATCAC CGTCCAGACA    2520
GTGACCTGGC CTGACATGGA GCTGCCACTG CCTCGAAACA TCACTGAGGG TGAAGCCCGA    2580
GGCAGCGTGA TCCTTACCGT AAAGCCCATC TTCGAGGTCT CCCCCAGTCC CCTGGAACCC    2640
GAGGAGCCCT TCACGTTTGC CCCTGAAATA GGGGCCACTG CCTTCGCTGA GGTTGAGAAT    2700
GAGACTGGAG AGGCCACCAG GCCCTGGGGC TTTCCCACAC CTGGCCTGGG CCCTGCCACG    2760
GCATTCACCA GTGAGGACCT CGTCGTGCAG GTGACCGCTG TCCCTGGGCA GCCGCATTTG    2820
CCAGGGGGAG GGGATCCCGA GGGTGAGTAC TAAGCTTCAG CGCTCCTGCC TGGACGCATC    2880
CCGGCTATGC AGCCCCAGTC CAGGGCAGCA AGGCAGGCCC CGTCTGCCTC TTCACCCGGA    2940
GGCCTCTGCC CGCCCCACTC ATGCTCAGGG AGAGGGTCTT CTGGCTTTTT CCCCAGGCTC    3000
TGGGCAGGCA CAGGCTAGGT GCCCCTAACC CAGGCCCTGC ACACAAAGGG GCAGGTGCTG    3060
GGCTCAGACC TGCCAAGAGC CATATCCGGG AGGACCCTGC CCCTGACCTA AGCCCACCCC    3120
AAAGGCCAAA CTCTCCACTC CCTCAGCTCG GACACCTTCT CTCCTCCCAG ATTCCAGTAA    3180
CTCCCAATCT TCTCTCTGCA GAGCCCAAAT CTTGTGACAA AACTCACACA TGCCCACCGT    3240
GCCCAGGTAA GCCAGCCCAG GCCTCGCCCT CCAGCTCAAG GCGGGACAGG TGCCCTAGAG    3300
TAGCCTGCAT CCAGGGACAG GCCCCAGCCG GGTGCTGACA CGTCCACCTC CATCTCTTCC    3360
TCAGCACCTG AACTCCTGGG GGGACCGTCA GTCTTCCTCT TCCCCCCAAA ACCCAAGGAC    3420
ACCCTCATGA TCTCCCGGAC CCCTGAGGTC ACATGCGTGG TGGTGGACGT GAGCCACGAA    3480
GACCCTGAGG TCAAGTTCAA CTGGTACGTG GACGGCGTGG AGGTGCATAA TGCCAAGACA    3540
AAGCCGCGGG AGGAGCAGTA CAACAGCACG TACCGTGTGG TCAGCGTCCT CACCGTCCTG    3600
CACCAGGACT GGCTGAATGG CAAGGAGTAC AAGTGCAAGG TCTCCAACAA AGCCCTCCCA    3660
```

FIG. 7C

```
GCCCCCATCG AGAAAACCAT CTCCAAAGCC AAAGGTGGGA CCCGTGGGGT GCGAGGGCCA    3720
CATGGACAGA GGCCGGCTCG GCCCACCCTC TGCCCTGAGA GTGACCGCTG TACCAACCTC    3780
TGTCCCTACA GGGCAGCCCC GAGAACCACA GGTGTACACC CTGCCCCCAT CCCGGGATGA    3840
GCTGACCAAG AACCAGGTCA GCCTGACCTG CCTGGTCAAA GGCTTCTATC CCAGCGACAT    3900
CGCCGTGGAG TGGGAGAGCA ATGGGCAGCC GGAGAACAAC TACAAGACCA CGCCTCCCGT    3960
GCTGGACTCC GACGGCTCCT TCTTCCTCTA CAGCAAGCTC ACCGTGGACA AGAGCAGGTG    4020
GCAGCAGGGG AACGTCTTCT CATGCTCCGT GATGCATGAG GCTCTGCACA ACCACTACAC    4080
GCAGAAGAGC CTCTCCCTGT CTCCGGGTAA ATGAGTGCGA CGGCCGCGAC TCTAGAGGAT    4140
CTTTGTGAAG GAACCTTACT TCTGTGGTGT GACATAATTG GACAAACTAC CTACAGAGAT    4200
TTAAAGCTCT AAGGTAAATA TAAAATTTTT AAGTGTATAA TGTGTTAAAC TACTGATTCT    4260
AATTGTTTGT GTATTTAGA TTCCAACCTA TGGAACTGAT GAATGGGAGC AGTGGTGGAA    4320
TGCCTTTAAT GAGGAAAACC TGTTTTGCTC AGAAGAAATG CCATCTAGTG ATGATGAGGC    4380
TACTGCTGAC TCTCAACATT CTACTCCTCC AAAAAAGAAG AGAAAGGTAG AAGACCCCAA    4440
GGACTTTCCT TCAGAATTGC TAAGTTTTTT GAGTCATGCT GTGTTTAGTA ATAGAACTCT    4500
TGCTTGCTTT GCTATTTACA CCACAAAGGA AAAAGCTGCA CTGCTATACA AGAAAATTAT    4560
GGAAAAATAT TCTGTAACCT TTATAAGTAG GCATAACAGT TATAATCATA ACATACTGTT    4620
TTTTCTTACT CCACACAGGC ATAGAGTGTC TGCTATTAAT AACTATGCTC AAAAATTGTG    4680
TACCTTTAGC TTTTTAATTT GTAAAGGGGT TAATAAGGAA TATTTGATGT ATAGTGCCTT    4740
GACTAGAGAT CATAATCAGC CATACCACAT TTGTAGAGGT TTTACTTGCT TTAAAAAACC    4800
TCCCACACCT CCCCCTGAAC CTGAAACATA AAATGAATGC AATTGTTGTT GTTAACTTGT    4860
TTATTGCAGC TTATAATGGT TACAAATAAA GCAATAGCAT CACAAATTTC ACAAATAAAG    4920
CATTTTTTTC ACTGCATTCT AGTTGTGGTT TGTCCAAACT CATCAATGTA TCTTATCATG    4980
TCTGGATCCT GTGGAATGTG TGTCAGTTAG GGTGTGGAAA GTCCCCAGGC TCCCCAGCAG    5040
GCAGAAGTAT GCAAAGCATG CATCTCAATT AGTCAGCAAC CAGGTGTGGA AAGTCCCCAG    5100
GCTCCCCAGC AGGCAGAAGT ATGCAAAGCA TGCATCTCAA TTAGTCAGCA ACCATAGTCC    5160
CGCCCCTAAC TCCGCCCATC CCGCCCCTAA CTCCGCCCAG TTCCGCCCAT TCTCCGCCCC    5220
ATGGCTGACT AATTTTTTTT ATTTATGCAG AGGCCGAGGC CGCCTCGGCC TCTGAGCTAT    5280
TCCAGAAGTA GTGAGGAGGC TTTTTGGAG GCCTAGGCTT TTGCAAAAAG CTAATTC      5337
```

US 6,180,334 B1

ARTIFICIAL RECOMBINANT SUBSTRATE (RAGG 1) AND NATIVE AGGRECAN TO DETERMINE THE PROTEOLYTIC ACTIVITY OF 'AGGRECANASE' IN CELL CULTURE SYSTEMS

This application is a divisional of application Ser. No. 08/784,512, filed Jan. 17, 1997, now U.S. Pat. No. 5,872, 209.

BACKGROUND OF THE INVENTION

Mechanisms of proteoglycan breakdown in connective tissue are complex and involve multiple agents and pathways. Aggrecan is the large aggregating chondroitin sulfate proteoglycan of cartilage. See, for example, Doege, et al. *J. Biol. Chem.* 266:894 (1991); GenBank/EMBL Accession Number M55172 (human aggrecan). In studies investigating the catabolism of aggrecan, experimental systems used have included monolayer cultures of primary chondrocytes from established chondrocyte cell lines (Hughes C E, et al., *Biochem. J.* (1995) 305:799–804; Lark M W et al., *J. Biol. Chem.* (1995) 270(6):2550–2556) and explant cultures using cartilage from a variety of anatomical sites and animal species (Flannery C R, et al. *J. Biol. Chem.* (1992) 267:1008–1014; Sandy J D, et al. *Biochim Biophys Acta* (1978) 543:536–44; Tyler J A, *Biochem. J.* 1985; 225:493–507). The addition of cytokines such as IL-1 and TNF have been extensively used as agents which promote the degradation of the extracellular matrix (Hughes C E et al., supra (1995) Morales T I, et al. *Arch Biochem Biophys* (1992) 293(1):79–84; Fosang A J, et al. *Matrix* (1991) 11:17–24).

In particular, these two cytokines have been shown to target the catabolism of aggrecan.

Several studies have now lead to a number of important discoveries which have defined specific cleavage sites along the protein core of aggrecan (Ilic M Z, et al. *Arch Biochem Biophys* (1992) 294(1):115–22; Loulakis P, et al. Putative site(s) of enzymic cleavage. *Biochem J* (1992) 284:589–593; Sandy J D, et al. *J. Biol. Chem.* (1991) 266:8683–8685). In total there appear to be at least seven cleavage sites, and amino acid sequence analysis of cartilage proteoglycan breakdown products have defined two major sites of proteolytic cleavage in aggrecan which occur within the interglobular domain (IGD) between amino acid residues $Asn^{341}$-$Phe^{342}$ ("AF") and $Glu^{373}$-$Ala^{374}$ ("EA") (human sequence enumeration). Doege K J, et al. *J. Biol. Chem.* (1991) 266:894–902. The AF cleavage site generates a C-terminal catabolic fragment (ending with the C-terminal sequence DIPEN) consisting of the 50–60 kDa G1 domain that remains in the tissue complexed to hyaluronate (Flannery C R, et al., 1992). In recent studies Fosang et al. (*Trans. Orthop. Res. Soc.* (1995)20:4) have also identified N-terminal fragments (beginning with the N-terminal sequence FFG) from this cleavage site in synovial fluids from patients diagnosed with a variety of different arthritides (joint disease). Similarly, Witt et al (*Trans. Orthop. Res. Soc.* 1995; 20:122) have found these glycosaminoglycan-containing N-terminal fragments in media samples from control and IL-1 stimulated porcine explant cultures.

The EA cleavage site produces glycosaminoglycan-containing N-terminal fragments (ARG . . . ) that appear as the major aggrecan degradation products isolated from synovial fluid of patients with arthritis (Lohmander LS, et al. *Arth. Rheum.* (1993) 36:1214–1222). These N-terminal fragments are also found in media from cartilage explant cultures treated with IL-1 or retinoic acid (Hughes C E, et al., 1995; Sandy J D, et al., 1991). A recent study (Lark M W, et al., 1995) identified the C-terminal fragment (ending with the C-terminal sequence EGE) in rat chondrosarcoma cells treated with retinoic acid.

The proteolytic activity responsible for this $Glu^{373}$-$Ala^{374}$ cleavage has not been identified but it appears to have specificity for Glu-Xaa peptide bonds where Xaa is Ala, Gly or Leu. This activity has been termed "aggrecanase." Fosang A J, et al. *J. Biol. Chem.* (1992) 267:19470–19474). As used in this specification, "aggrecanase" means a polypeptide (or polypeptides) that will catalyze cleavage of such Glu-Xaa peptide bonds in aggrecan. Although the sites of cleavage within the molecule have been well characterized, many of the agents responsible for generating the large number of different proteoglycan degradation products are still unidentified. It is believed that more than one enzyme is responsible for degradation of proteoglycans. Culture systems have been manipulated with a variety of agents that enhance proteoglycan catabolism, in an effort to discover the agent(s) responsible for its breakdown. However, these studies have been unsuccessful in defining any specific agent responsible for the degradation of aggrecan. Flannery C R, et al. *Trans. Orthop. Res. Soc.* (1993). Nonetheless, experimental data using purified aggrecan and modified aggrecan as a substrate for purified enzyme preparations has yielded some information on the specific cleavage sites of the enzymes involved in proteoglycan degradation. However, this in vitro work has not definitively ascertained the mechanism or identity of agents involved in the degradation of aggrecan in cartilage. Fosang A J, et al. (1992); Fosang A J, et al. *J. Biol. Chem.* (1991) 266:15579–15582; Fosang A J, et al., *Biochem. J.* (1994) 304:347–351.

In previous studies (Hughes C E, et al., supra, (1995); Hughes C E, et al. *J. Biol. Chem.* (1992) 267:16011–16014) a number of monoclonal antibodies have been developed that are specific for the products (proteoglycan aggregate catabolites) that have been cleaved by specific proteinases. These antibodies have proved useful as tools in studying the mechanisms of breakdown of proteoglycan in cartilage explant culture systems, by allowing monitoring of specific cleavage products.

SUMMARY OF THE INVENTION

In one embodiment, the invention provides an isolated recombinant polypeptide substrate for aggrecanase. In another embodiment, the invention provides a recombinant substrate for aggrecanase that comprises the following components, beginning with the N-terminus and ending with the C-terminus:

a) the signal sequence of CD5;

b) the FLAG-epitope;

c) the interglobular domain of human aggrecan;

d) the hinge region of human IgG1;

e) the CH2 region of human IgG1; and f) the CH3 region of human IgG1.

In another embodiment, the invention relates to a recombinant substrate for aggrecanase that comprises the amino acid sequence as set forth in FIG. 6 (SEQ. ID NO. 3). In yet another embodiment, the invention relates to a recombinant substrate that comprises a portion of the amino acid sequence as set forth in FIG. 6 (SEQ. ID NO. 3).

In a further embodiment, the invention relates to a recombinant substrate for aggrecanase that comprises the amino acid sequence as set forth in FIG. 6 (SEQ. ID NO. 3) and wherein amino acid 34 is mutated to Ala. In yet a further embodiment, the invention relates to a recombinant substrate for aggrecanase that comprises a portion of the amino acid sequence as set forth in FIG. 6 (SEQ. ID NO. 3) and wherein amino acid 34 is mutated to Ala.

In another embodiment, the invention relates to an isolated DNA sequence encoding a recombinant substrate for aggrecanase. In a further embodiment, one such DNA sequence comprises the nucleotide sequence of nucleotides 2350 to 4114 of FIG. 7 (SEQ. ID NO. 4). In another embodiment, another such DNA sequence comprises a portion of the nucleotide sequence of nucleotides 2350 to 4114 of FIG. 7 (SEQ. ID NO. 4). In yet a further embodiment, the invention relates to a DNA sequence encoding a substrate for aggrecanase, wherein said DNA sequence hybridizes under stringent conditions with the nucleotide sequence of nucleotides 2350 to 4114 of FIG. 7 (SEQ. ID NO. 4).

The invention also relates to a vector comprising a DNA sequence encoding a recombinant substrate for aggrecanase. In another embodiment, the invention relates to a host cell comprising such a vector. In a further embodiment, the invention relates to a vector comprising the nucleotide sequence set forth in FIG. 7 (SEQ ID NO:4).

In still another embodiment, the invention relates to a cell culture system (or method) for monitoring aggrecanase activity in a sample comprising:

(a) mixing freshly isolated chondrocyte cells and a recombinant substrate for aggrecanase;

(b) incubating the reaction mixture of step (a); and (c) detecting the presence or absence of aggrecanase activity in the reaction mixture, wherein aggrecanase activity is determined by the presence of aggrecanase peptide cleavage products.

In one embodiment, such a system is free of endogenous proteoglycans or other extracellular components.

In another embodiment, the presence or absence of cleavage products is measured in such a system by determining the presence of peptide cleavage products that react with monoclonal antibodies specific for aggrecanase cleavage products. In a further embodiment, the monoclonal antibody detects a peptide having an amino acid sequence ARGSV. In yet another embodiment, the aggrecanase activity of the chondrocytes in such a system is stimulated by adding retinoic acid to the reaction mixture of step (a).

The invention further relates to a method for cloning aggrecanase cDNA comprising:

(a) preparing a cDNA expression library from cells expressing aggrecanase;

(b) transfecting suitable cells with the library of step (a), wherein said cells express said cDNA;

(c) incubating the cells of step (b) with a recombinant substrate for aggrecanase; and (d) detecting the presence of an aggrecanase cleavage product produced by a cell of step (c).

In still another embodiment, the invention relates to a method for screening for an aggrecanase inhibitor, comprising:

(a) mixing freshly isolated chondrocyte cells and a recombinant substrate for aggrecanase;

(b) incubating the reaction mixture of step (a) in the presence or absence of a putative aggrecanase inhibitor; and (c) detecting the presence or absence of aggrecanase activity in the reaction mixture, wherein aggrecanase activity is determined by the presence of aggrecanase peptide cleavage products.

In still another embodiment, the invention relates to a method for monitoring the onset of osteoarthritis, said method comprising assaying a sample of biological fluid from a patient for the presence of aggrecanase, wherein said aggrecanase activity is measured using a system described above. In another embodiment, the invention relates to such a monitoring method wherein said biological fluid is selected from the group consisting of synovial fluid, urine, serum, and lymph fluid.

In another embodiment, the invention relates to a method for monitoring the progression of osteoarthritis, said method comprising assaying a sample of biological fluid from a patient suffering from osteoarthritis for the presence of aggrecanase, wherein said aggrecanase activity is measured using a system as described above. In another embodiment, the invention relates to such a monitoring method wherein said biological fluid is selected from the group consisting of synovial fluid, urine, serum, and lymph fluid. In still another embodiment, the invention relates to such a monitoring method, wherein said method is used to follow disease progression to determine the effectiveness of therapeutic treatment.

Another embodiment of the present invention is a diagnostic aid comprising a recombinant substrate for aggrecanase and antibodies for the detection of aggrecanase cleavage products.

BRIEF DESCRIPTION OF THE DRAWINGS

FIGS. 3A–3C show SDS-PAGE of purified rAGG-1. Lane A: Coomassie staining; lane B: Western blot detection with monoclonal antibody M1 and anti-human IgG antiserum, lane C.

FIGS. 6A and 6B show the amino acid sequence of the recombinant polypeptide substrate rAGG-1—Amino acids 1–24: CD5 signal sequence; Amino acids 25–32:Flag-sequence; Amino acids 33–160: Human aggrecan interglobular domain; Amino acids 161–164: Spacer sequence; Amino acids 165–179: Hinge region of human IgG1; Amino acids 180–289: CH2 region of human IgG1; Amino acids 290–396: CH3 region of human IgG1.

FIGS. 7A–7C show the nucleotide sequence of vector prAGG-1-IGG (pCDM8-rAGG-1) for eucaryotic expression of rAGG-1.

DETAILED DESCRIPTION OF THE INVENTION

Figure 1:
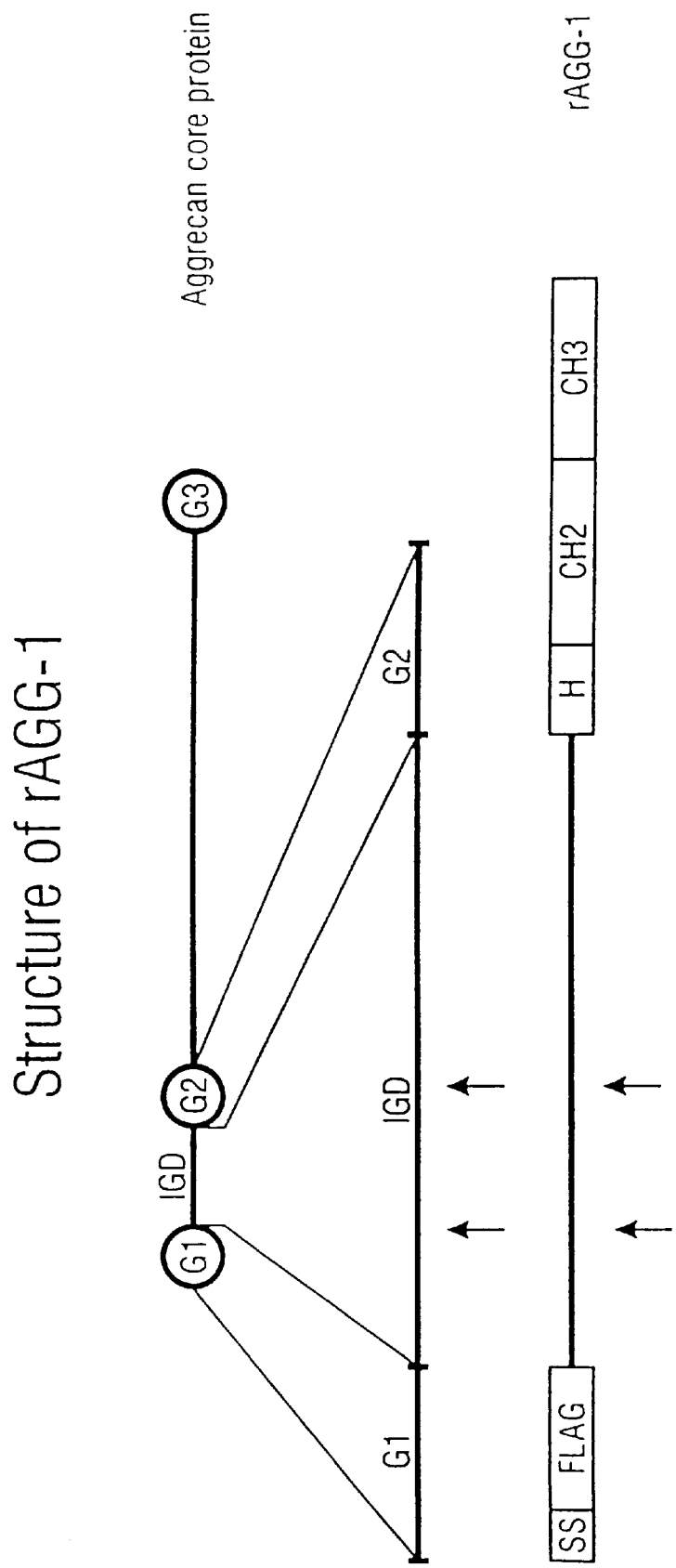
FIG. 1 shows the overall structure of rAGG-1. rAGG-1 consists of: Signal sequence of CD5 (SS); FLAG-epitope for M1 monoclonal antibody detection (FLAG); interglobular domain of human aggrecan (IGD); hinge region of human IgG1 (H); CH2 region of human IgG1 (CH2); CH3 region of human IgG1 (CH3).
Figure 2:
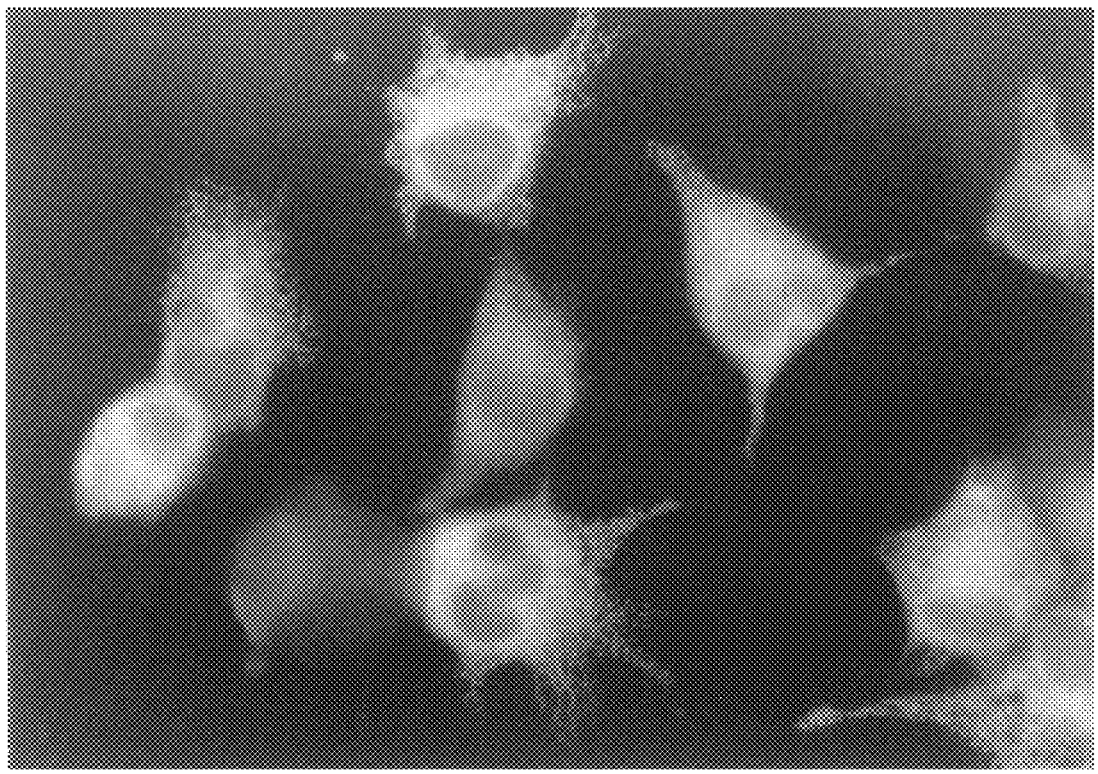
FIG. 2 shows detection of rAGG-1 expression in COS cells with monoclonal antibody M1.
Figures 4A, 4B, 4C:
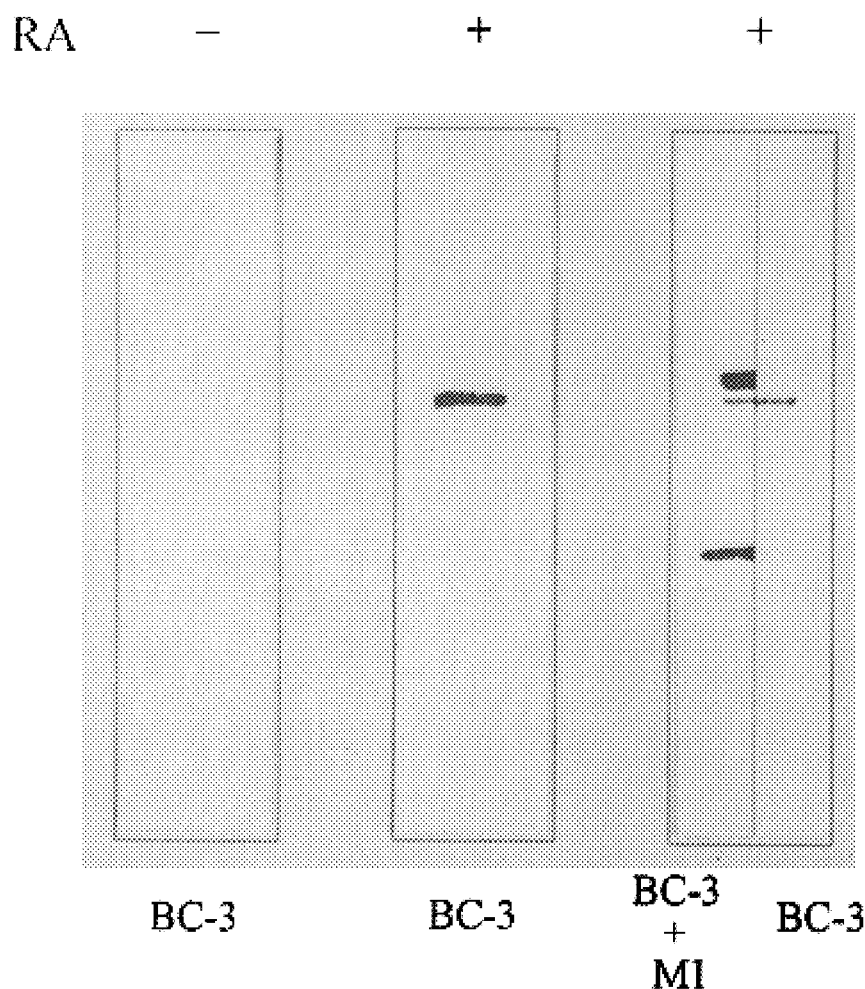
FIGS. 4A–4C show BC-3 reactivity of rAGG-1 in cell culture medium from rat chondrosarcoma cells. Lane A: rAGG-1 from a culture of unstimulated rat chondrosarcoma cells is not detected with BC-3 monoclonal antibody on a western blot, whereas rAGG-1 from a culture of retinoic acid stimulated cells is detected as shown in lane B. Lane C: A similar blot, after reprobing with monoclonal antibody M1. The BC-3 reactive fragment is approximately 5.6 kD smaller than the original 72 kD band, indicating the cleavage of rAGG-1 at the "aggrecanase" site.
Figure 5:
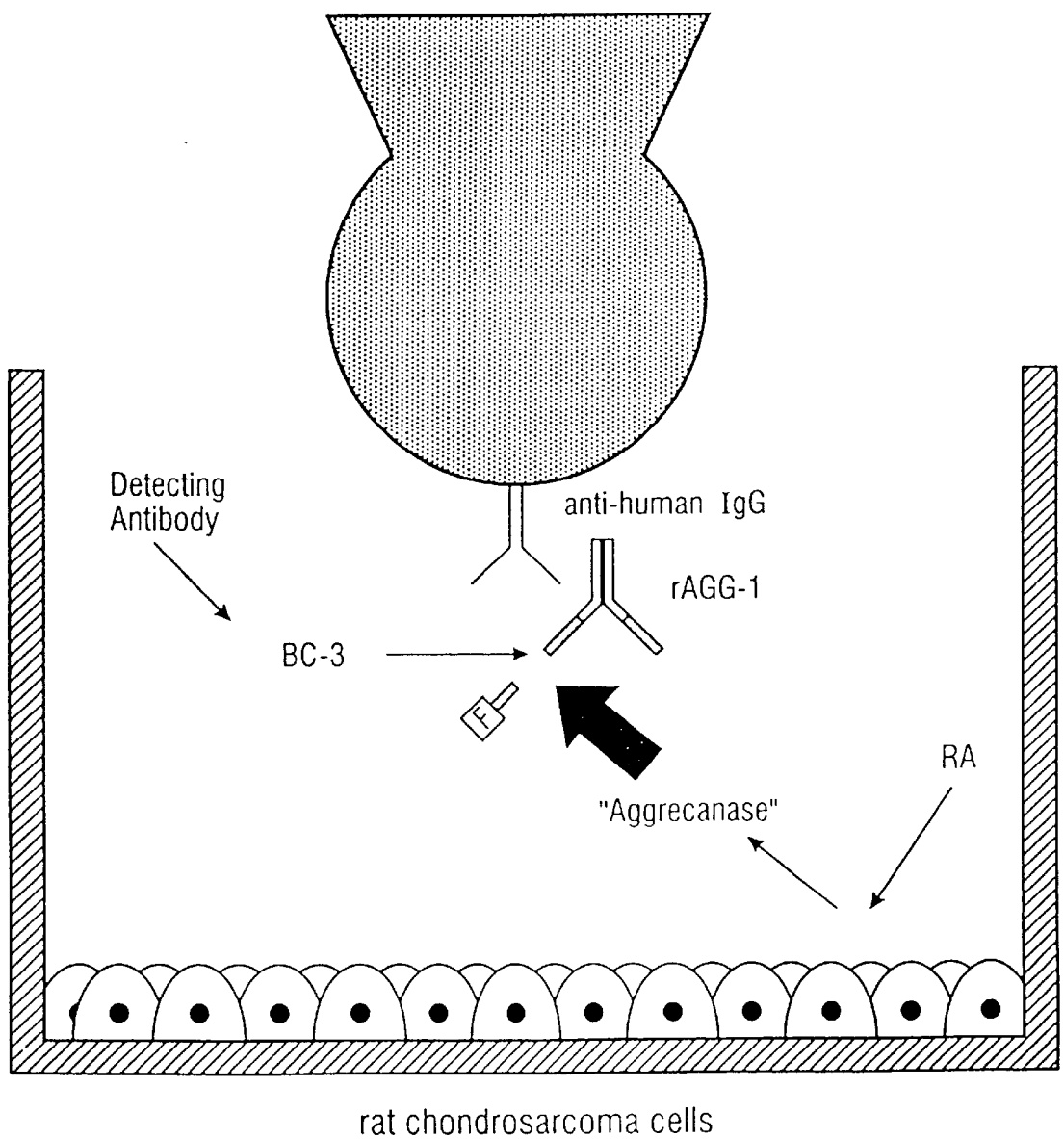
FIG. 5 shows set up of a 96 well format screening assay (with pin lid) to detect "aggrecanase" activity.

The present invention refers to a recombinant polypeptide substrate (rAGG1) and native aggrecan for the study of the proteolytic activity of "aggrecanase" in cell culture systems. As used in this specification, a "recombinant polypeptide substrate" for aggrecanase means a polypeptide that can be cleaved by aggrecanase and that is a non-naturally occurring protein. This invention provides, for the first time, the production and use of an recombinant polypeptide substrate for the study of 'aggrecanase' activity. This invention further refines culture systems that will help facilitate the identification of the agents responsible for the cleavage of aggrecan at the $^{374}$ARGSVI . . . site in the IGD of aggrecan.

The present application describes the development of an in vitro cell culture system (or method) that has enabled study of the activity of "aggrecanase" against a recombinant polypeptide substrate in a cell culture system that is free of inherent endogenous proteoglycans and other extracellular components. As used in this specification, "free of" is used to mean that such proteoglycans and other components are present in a concentration low enough so that they do not significantly compete with the recombinant substrate in the aggrecanase assay. An "endogenous proteoglycan," as used in this specification, refers to those proteglycans produced by the cells in a cell culture system. "Other extracellular components" is used to refer to large molecular weight molecules made by cells in such a cell culture system that are secreted into the medium or retained on the cell surface. Examples of such components are proteoglycans and high molecular weight proteins and glycoproteins. The use of previously characterized neoepitope antibodies to key cleavage sites in the IGD of aggrecan facilitated the monitoring of products generated by the proteolytic action of "aggrecanase" in this system.

Therefore, an embodiment of the present invention is a recombinant polypeptide substrate for aggrecanase in vitro testing systems. In one embodiment, there is provided a recombinant polypeptide substrate which contains a group of structural elements comprising a) the signal sequence of CD5, b) the FLAG-epitope, c) the interglobular domain of human aggrecan, d) the hinge region of human IgG1, e) the CH2 region of human IgG1 and f) the CH3 region of human IgG1.

The FLAG epitope can be identified by the M1 monoclonal antibody. Regarding element (c), the interglobular domain of aggrecan from a non-human species can also be used. Full length cDNAs have been reported for the following species: rat (GenBank J03485; Doege, et al. *J. Biol. Chem.* 262:17757 (1987)) and mouse (GenBank U22901; Watanabe, et al. *Biochem. J.* 308:433 (1995)). Partial cDNA sequences have been reported for the following species: chicken (Sai et al. *PNAS USA* 83:5081 (1986); Kruger et al. *J. Biol. Chem.* 265:12088 (1990) and bovine (GenBank Y00319, J05028).

In one embodiment of the invention, these elements form a fusion protein, beginning with the N-terminus, comprising elements a, b, c, d, e, and f (a-b-c-d-e-f).

Another embodiment of the present invention is a recombinant substrate which has the amino acid sequence of FIG. 6 (SEQ. ID NO. 3). In yet another embodiment, the invention provides such a substrate having a portion of the amino acid sequence of FIG. 6 (SEQ. ID NO. 3). In yet another embodiment, the invention provides a substrate having the amino acid sequence of FIG. 1 (SEQ. ID NO. 3), wherein the amino acid 34 is mutated to Ala. In still another embodiment, the invention provides such a mutated substrate having a portion of the amino acid sequence of FIG. 1 (SEQ. ID NO. 3), wherein the amino acid 34 is mutated to Ala.

Another embodiment of the present invention is a nucleotide sequence, such as DNA, encoding a recombinant polypeptide substrate according to the invention. In one embodiment, the invention provides a DNA sequence having the nucleotide sequence of nucleotides 2350 to 4114 of FIG. 7 (SEQ. ID NO. 4). In another embodiment, the invention provides a DNA sequence having a portion of the DNA sequence of FIG. 7 (SEQ. ID NO. 4). In yet another embodiment, the invention provides the nucleotide sequence of nucleotides 2350 to 4114 of FIG. 7 (SEQ. ID NO. 4), wherein nucleotide 2448 is mutated to C, nucleotide 2450 is mutated to C and nucleotide 2451 is mutated to A. In yet another embodiment, the invention provides a portion of the nucleotide sequence of nucleotides 2350 to 4114 of FIG. 7 (SEQ. ID NO. 4), wherein nucleotide 2448 is mutated to C, nucleotide 2450 is mutated to C and nucleotide 2451 is mutated to A.

In still another embodiment, the invention provides a nucleotide sequence which hybridizes under stringent conditions with the DNA sequence shown in FIG. 7 (SEQ. ID NO. 4). Hybridization under stringent conditions according to the invention means hybridization at a temperature of 20 to 25° C., or about 20 to 25° C., under the melting point ($T_m$) formed between a probe and its target, in a hybridization solution containing 6×SSC (or alternatively 6×SSPE), 0.5% SDS and 100 µg/ml denatured, fragmented Salmon sperm DNA (Sambrook et al., "Molecular Cloning-A Laboratory Manual", Second Edition, 1989, Cold Spring Harbor Laboratory Press, Volume 2, chapter 9, pages 9.52–9.55, hereby incorporated by reference). The skilled artisan will recognize that the $T_m$ of a probe and its target may be estimated using the equation at the top of page 9.51 of Sambrook.

In other embodiments, the present invention provides a vector containing a DNA fragment comprising a nucleotide sequence as described above (encoding a recombinant polypeptide substrate for aggrecanase) and a host cell containing said vector. Suitable vectors include, but are not limited to pCDM8, pCDNAI, pCDNAIII, pEUK-C1, and pMAM. Suitable host cells include, but are not limited to COS, COS-7, CHO, BHK, and HeLa.

In another embodiment, the invention provides a cell culture system for monitoring aggrecanase activity in a sample comprising (1) mixing freshly isolated chondrocyte cells and a substrate according to the invention; (2) incubating the reaction mixture; and (3) detecting the presence or absence of aggrecanase activity in the reaction mixture, wherein aggrecanase activity is determined by the presence of aggrecanase peptide cleavage products. The presence or absence of cleavage products is measured by determining the presence of peptide cleavage products that react with monoclonal antibodies that are specific for aggrecanase cleavage products. Aggrecanase cleavage products are fragments of the recombinant substrate, which have the aminoterminus ARGSV. A monoclonal antibody that is "specific for an aggrecanase cleavage product" will spefically detect such cleavage products. For example, antibody BC-3 detects the amino terminus, ARGSV, on aggrecan degradation products. Hughes, et al. *Biochem. J.* 305:799 (1995). The skilled artisan will recognize that other monoclonal antibodies that are specific for aggrecanase cleavage products can be made using procedures that are well known to the skilled artisan. See, for example, Hughes, et al. *J. Biol Chem.* 267:16011 (1992).

The skilled artisan will recognize that the length of the incubation of the reaction mixture containing substrate and cells will vary according to experimental conditions. Suitable reaction conditions include, but are not limited to the following procedure: Cells such as rat chrondrosarcoma cells or primary bovine chondrocytes are grown embedded in FMS Seaplaque agarose in DMEM medium at about 37° C. at a density of about $2 \times 10^6$ cells/ml in 24 well culture plates. 20µ recombinant substrate is added into the DMEM medium and the culture medium is brought to about $10^{-6}$M retinoic acid. Culture are kept for 48–96 hours at about 37° C. The medium will contain fragments of the recombinant substrate with the aminoterminus ARGSV, which can be quantified.

In one alternative embodiment, the cell culture system is free of inherent endogenous proteoglycans and other extracellular components. Thus, this novel cell culture system allows monitoring of "aggrecanase" activity without the complication of endogenous aggrecan acting as a substrate. In addition, freshly isolated chondrocytes can be used in this method without the need to establish an endogenous extracellular matrix to act as a substrate for any 'aggrecanase' activity. Prior art methods relied on an established extracellular matrix for assaying "aggrecanase" activity, such as aggrecan G1–G2 domains from pig laryngeal cartilage. See Hughes, et al. *J. Biochem.* 305:799 (1995).

Newly developed culture systems according to the invention will prove useful for further studies of the molecular mechanisms involved in aggrecan degradation by "aggrecanase." It is also a novel experimental approach that for studies of the catabolism of other matrix macromolecules (such as link protein, brevican, other proteoglycans and collagens) given the availability of recombinant polypeptide substrates and neoepitope antibodies.

A further embodiment of the present invention is a method as described above, wherein the study of the activity of aggrecanase is performed by detection of cleavage products by antibodies that are specific for certain cleavage products.

Another embodiment of the present invention is a method for the detection of new enzymatic cleavage sites in a recombinant polypeptide substrate, comprising using a recombinant substrate according to the invention in a suitable system for measuring enzymatic activity. The substrate is incubated with an enzyme, such as aggrecanase, under varying conditions and the cleavage products are analyzed. Peptide-specific monoclonal antibodies such as BC-3 or BC14 are used to determine the identity of cleavage products. Alternatively, cleavage products are purified using techniques well-known to the skilled artisan and are subjected to N-terminal sequence analysis.

Another embodiment of the present invention is a method for the purification of aggrecanase by means of affinity chromatography using a recombinant substrate according to the invention, linked to an affinity matrix.

In yet another embodiment, the recombinant substrate is used together with the antibody BC-3 to monitor aggrecanase activity during purification of aggrecanase activity. Thus, enrichment of aggrecanase in a sample is measured by the ability of such a sample to catalyze breakdown of a recombinant substrate according to the invention by monitoring with BC-3 antibody. Suitable methods for such purification include ion exchange chromatography, gel filtration chromatography, and other techniques that are well known to the skilled artisan.

In yet another embodiment, the invention provides a functional cloning system for the isolation of aggrecanase cDNA. In such a system, an "expression library" is plated on medium containing a recombinant polypeptide substrate according to the invention. A suitable expression library is prepared from retinoic acid-stimulated rat chondrosarcoma cells in the plasmid pCDM8. Cells, such as COS-7 cells, are transfected with this library and plated in 96 well culture plates. The recombinant substrate is added into the medium of the culture plates the plates are incubated for at least about 48 hours to allow for cleavage of the substrate by aggrecanase. Cleavage of substrate at an "aggrecanase" site will be indicated by reactivity of expression products with the BC-3 antibody, and will indicate the presence of a clone containing cDNA encoding "aggrecanase" activity.

In yet another embodiment, the invention provides a method for monitoring the onset or progression of osteoarthritis, said method comprising assaying a sample of biological fluid, from a human suspected or known to have osteoarthritis, for the presence of aggrecanase by means of the recombinant polypeptide substrate as described above, wherein said biological fluid is selected from the group consisting of synovial fluid, urine, serum, and lymph fluid. It is known that the presence of "aggrecanase" activity in one or more of such fluids is correlated with the onset and progression of osteoarthritis and rheumatoid arthritis, with "aggrecanase" activity increasing as the disease progresses.

Thus, an additional embodiment of the present invention is a "monitoring" method as described above, wherein said method is used to follow disease progression to determine the effectiveness of a treatment. As the effectiveness of treatment increases, "aggrecanase" activity will decrease.

Another embodiment of the present invention is a method for the screening for an aggrecanase inhibitor, comprising the following steps. Suitable cells, such as rat chondrosarcoma cells, are cultivated in agarose in 96 well plates in medium (such as DMEM) and stimulated with retinoic acid to induce expression of aggrecanase. The recombinant substrate is attached to the surface of plastic pins of plastic lids for 96 well plates (such as NUNC TSP plates). The substrate is incubated in the medium (with or without a potential aggrecanase inhibitor) for a suitable time to allow cleavage by aggrecanase (e.g., for about 48 hours). The attachment of the substrate is achieved via binding the carboxyterminal immunoglobulin domain of the substrate anti-human IgG antibodies non-specifically adsorbed to the plastic of the pins. ARGSV-neoepitopes produced by the aggrecanase action on the recombinant substrate is detected via immunodetection with an ARGSV-specific monoclonal antibody (such as BC-3). The amount of bound BC-3 antibody is quantified via detection with goat anti-mouse IgG peroxidase antibody and a suitable color substrate.

The skilled artisan will recognize that aggrecanase inhibitors will decrease the formation of ARGSV-neopeptide, compared with control conditions (no inhibitor present).

Thus, in another embodiment of the present invention, the above-described method for monitoring aggrecanase activity is used to measure the amount of aggrecanase activity in a tissue or fluid sample from a patient. For example, the synovial fluid from the knee of a patient is placed into a 96-well plate and the bound substrate, as described above, is added to the fluid samples. Aggrecanase activity is determined by immunodetection with BC-3 antibody.

Another embodiment of the present invention is a diagnostic aid comprising a recombinant polypeptide substrate as described above and antibodies for the detection of aggrecanase cleavage products. As described above, following cleavage of the recombinant substrate, antibody, such as BC-3, can be added to quantify the amount of aggrecanase activity.

The following examples are added to illustrate the present invention and do not serve to limit the scope of the present invention.

EXAMPLES

Materials: Alkaline phosphatase-conjugated second antibody and substrate used in Western blot analysis were obtained from Promega as the Protoblot Western blot AP system (catalog no. W3920). Nitrocellulose (0.2-$\mu$m pore size) was obtained from Schleicher and Schuell. Monoclonal antibody M1 and Anti-FLAG M1 Affinity gel were both obtained from Kodak. The M1 antibody recognizes the eight-amino acid FLAG epitope. Anti-Human Ig monoclonal was obtained from Capell, Durham. Monoclonal antibodies BC-3, 2-B-6 and 3-B-3 were prepared as ascitic fluid. Monoclonal antibody BC-3 recognizes the amino acid sequence ARGSV in human aggrecan and was prepared using the procedure described in Hughes, et al., 1995, Biochem. J. 305:799 (1995), hereby incorporated by reference. Monoclonal antibody 2-B-6 recognizes aggrecan proteoglycan core protein catabolites containing 4-sulfated oligosaccharide stubs and can be obtained commercially from ICN, order #69-622-2. See Caterson, et al., Biochem. Soc. Trans. 18:820 (1990), hereby incorporated by reference. Monoclonal antibody 3-B-3 recognizes unsaturated terminal disaccharide 6 which is sulfated on the aggrecan core protein and 30 is commercially available from ICN, order #69-621-2. See Couchman, et al. Nature 307:650 (1984). The Rx cell line was provided by Dr. Jim Kimura, Bone Research Center, Henry Ford Hospital, Detroit, Mich.

Example 1
Preparation of the rAGG1 Genetic Construct

The genetic construct for rAGG1 codes for the signal sequence of the lymphocyte glycoprotein T1/Leu-1 (CD5), the eight amino acid long FLAG™ epitope (Prickett K S, Amberg D C, Hopp T P, Bio Techniques 1989; 7:580–589), the 127 amino acid long interglobular domain of the human cartilage large aggregating proteoglycan aggrecan ($^{350}$T-$^{476}$G) (Doege K J, et al., 1991), a two amino acid long glycine spacer and the human IgG1 hinge, CH2 and CH3 constant regions, thus giving rise to a fusion protein with an expected molecular mass of 41,059 daltons.

Aggrecan cDNA sequences encoding the interglobular domain were amplified by the reverse transcriptase polymerase chain reaction (RT-PCR) (Beverly S M, Current Protocols in Molecular Biology. Canada: John Wiley and Sons, 1992) with synthetic oligonucleotides complementary to sequences flanking this region and human knee cartilage total RNA. Total RNA was extracted from human cartilage tissue, obtained from joint replacement surgery, according to Adams et al (Adams M E, Huang D Q, Yao L Y, Sandell L J, Anal. Biochemistry 1992; 202:89–95).

Oligonucleotides were designed to contain additional sequence information regarding the FLAG epitope and the g-spacer and to allow the creation of restriction enzyme cleavage sites at the 5' and 3' extremities of the amplified cDNA segments to facilitate subsequent insertion into the CD5-IgG1 expression vector, modified to contain a 3' NheI site. See Aruffo A, Stamenkovic I, Melcick M, Underhill C B, Seed B, Cell 1990; 61:1303–1313, hereby incorporated by reference. The primer encoding the FLAG epitope and the amino terminal start of the interglobular domain and including an NheI site was synthesized with the following sequence: 5'-CGC GGG GCT AGC CGA CTA CAA GGA CGA CGA TGA CAA GAC AGG TGA AGA CTT TGT GGA C (SEQ ID NO: 1). A reverse primer encoding the carboxyterminal end of the interglobular domain, the G-spacer, a splice donor site containing a BamHI site had the sequence: 5'-CGC GGG GGA TCC CCT CCC CCT GGC AAA TGC GGC TGC CC (SEQ ID NO: 2). The PCR product was produced using human cartilage total RNA as template and was digested with NheI and BamHI and ligated to NheI and BamHI-cut vector CD5-IgG (Aruffo A, et al., 1990). The sequence of the resulting vector, prAGG-1-IGG (pCDM8-rAGG-1), is given SEQ ID NO:4.

Example 2
Production and Purification of rAGG-1 in COS Cells

The prAGG-1-IGG construct was transfected into COS cells via DEAE-dextran (Hollenbaugh D, Aruffo A, Current protocols in molecular biology. Canada: John Wiley and Sons, 1994). Twelve hours after transfection, cells grown in DMEM, 10% FCS, were trypsinized, seeded onto fresh dishes and allowed to grow for five days. On the third day, fresh media and 10% FCS was added. Supernatants were harvested, centrifuged to remove nonadherent cells and debris, pooled and stored at 4° C. Fusion proteins were affinity purified via anti-FLAG™ M1 affinity gel (Kodak, New Haven) according to the manufacturer's protocol. Usually the yield was 1–5 $\mu$g fusion protein per ml of culture supernatant.

Example 3
Characteristics of the Recombinant IGD Construct

Transfection of the recombinant IGD construct into COS cells resulted in the cellular expression and subsequent secretion of the recombinant IGD product into the media. The use of an anti-FLAG M1 affinity gel facilitated its purification from transfected cell media. One liter of transfected COS cell media yielded 1–5 mg of recombinant IGD substrate. Under non-reducing conditions this recombinant IGD substrate formed large molecular weight aggregates due to the presence of an uneven number of cysteine residues in the immunoglobulin domain of the molecule. This aggregate formation facilitated immobilization of the recombinant IGD substrate in the agarose cultures. Under reducing conditions the recombinant IGD construct occurred as two molecular weight components having estimated Mr of 72 kDa and 39 kDa, as seen after separation on 10% SDS-PAGE gels. The reasons for the occurrence of two forms of the recombinant IGD substrate are currently unknown, however, both the anti M1 monoclonal (recognizing an epitope in the FLAG region of the construct) and the anti Ig monoclonal (recognizing an epitope in the immunoglobulin region of the construct) immunolocated both forms of the recombinant IGD construct. Densitometric analysis of a Coomassie stained gel of the separated recombinant IGD construct showed that the ratio of the 72 kDa to the 39 kDa band was approximately 10:1.

Example 4
Culture of Rat Chondrosarcoma Cells in Agarose in the Presence or Absence of Retinoic Acid for Studies of the Catabolism of the Recombinant IGD Substrate and Native Aggrecan Rat chondrosarcoma cells (cell line: Swarm rat chondrosarcoma cell line Rx) were plated in 75 cm$^2$ flasks and maintained in DMEM media containing 5% FCS and 50 $\mu$g/ml gentamicin. Confluent monolayers in 75 cm$^2$ flasks were harvested by trypsinization (0.25% trypsin in DMEM containing EDTA) for 15–20 minutes at 37° C. with agitation followed by digestion in 0.05% collagenase in DMEM for 1–2 hours. The cells were then resuspended in DMEM at 4×10$^6$ cells/ml. 24 well culture plates were 'coated' (200 $\mu$l/well) with a 1% (w/v) solution of FMC Seaplaque agarose in DMEM and the agarose solidified by incubation at 4° C. for 30 minutes (Aydelotte M B, Juettner K E, Conn. tissue Res. 1988; 18:205–222). The plates were then equilibrated to 37° C.

The rat chondrosarcoma cell suspension (described above) was diluted with a 2% solution of Seaplaque agarose in DMEM such that the final cell concentration was $2 \times 10^6$ cells/ml. 200 µl ($0.4 \times 10^6$ cells) of the agarose cell suspension was laid over the previously prepared agarose plugs and immediately following this, 50 µg of recombinant IGD substrate (rAGG1) or native bovine aggrecan (A1D1) was added to the appropriate wells and mixed by agitation. The plates were then incubated at 4° C. for 15 minutes to solidify the agarose. Experimental media (with or without retinoic acid) was then added to triplicate wells containing the recombinant IGD construct, native bovine aggrecan (A1D1) and cells alone as follows: Control cultures, DMEM+ gentamicin (50 µg/ml) and treated cultures, DMEM+ gentamicin (50 µg/ml)+$10^{-6}$ M retinoic acid (Hughes C E, et al., 1995). Agarose cell cultures were then maintained at 37° C. in 5% $CO_2$ for 96 hours after which media and agarose-cell matrix extracts were further analyzed. Upon stimulation with retinoic acid, these rat chondrosacroma cells (RX) are known to produce "aggrecanase," as evidenced by the ability of RA-stimulated cells to degrade aggrecan. See Lark et al., *J. Biol. Chem.* 270:2550 (1995, hereby incorpoared by reference.

Example 5
Analysis of Experimental Media From Control and Retinoic Acid Stimulated Agarose Cultures Media from the recombinant IGD substrate cultures and the cultures containing cells alone were dialyzed exhaustively against deionized $H_2O$ ("d.$H_2O$"), lyophilized and reconstituted in an equal volume of SDS-PAGE sample buffer containing 10% (v/v) mercaptoethanol. Media samples from the A1D1 cultures and the cultures containing cells alone were dialyzed into 0.1M Tris, 50 mM sodium acetate, pH 6.5 and deglycosylated using methods previously described (Hughes et al., 1995, supra.). Native A1D1 was deglycosylated to remove any potential BC-3 epitopes that were exposed in A1D1 prior to treatment with aggrecanase. Deglycosylation of a recombinant substrate according to the invention is not necessary.

The samples were then dialyzed exhaustively against d.$H_2O$, lyophilized and reconstituted in an equal volume of SDS-PAGE sample buffer. Samples (equal volumes/well) were then subjected to SDS-PAGE, transferred to nitrocellulose and immunolocated with either polyclonal or monoclonal antibodies using procedures described below.

Example 6
Extraction of Agarose-cell Matrix From Control and Retinoic Acid Stimulated Cultures Agarose plugs from recombinant IGD substrate cultures, bovine A1D1 cultures and cultures containing cells alone were extracted for 24 hours at 4° C. with 4M guanidinium chloride containing the following enzyme inhibitors: 10 mM EDTA, 5 mM benzamidine hydrochloride, 0.1M 6-aminohexanoic acid and 1 mM phenylmethanesulphonyl fluoride. The residue of the agarose gel was removed by centrifugation and the supernatants were then processed for each of the substrates as described above. Samples (equal volumes/well) were then subjected to SDS-PAGE, transferred to nitrocellulose and immunlocated with polyclonal and monoclonal antibodies using procedures described below.

Example 7
SDS-Polyacrylamide Gel Electrophoresis and Western Blot Analyses

Samples containing native recombinant IGD substrate and its catabolites were electrophoresed on 10% polyacrylamide slab gels in SDS using procedures described by Laemmli (Laemmli U K, Nature 1970; 227:680–685). After electrophoresis the fractionated proteins were electrophoretically transferred to nitrocellulose and immunolocated with anti-FLAG monoclonal or anti human immunoglobulin or monoclonal antibody BC-3 (all at a dilution of 1:1000) using procedures previously described (Hughes C E, et al., 1995). Samples containing native bovine A1D1 and its catabolites were electrophoresed on 3–15% SDS-PAGE gels and transferred to nitrocellulose membranes for immunolocation with a 1:1000 dilution of monoclonal antibodies 3-B-3; 2-B-6 and BC-3. In general, the immunoblots were incubated with substrate for 5–15 min at room temperature to achieve optimum color development.

Example 8
Immunochemical Analysis of the IGD Recombinant Construct From Agarose Cultures Treated with and without Retinoic Acid Recombinant IGD substrate was immobilized in agarose cell cultures containing rat chondrosarcoma chondrocytes, with or without retinoic acid, for 96 hours. Analysis of the IGD recombinant substrate and its metabolites in the culture media was examined by SDS-PAGE and Western Blot analysis. Immunolocation with anti M1 (recognizing an epitope in the FLAG domain at the N-terminal of the recombinant polypeptide substrate) showed no differences in the pattern of rAGG-1 metabolites present in media from either control cultures or retinoic acid treated cultures. However, immunolocation with anti Ig (recognizing an epitope in the immunoglobulin domain at the C-terminal of the recombinant polypeptide substrate) showed the presence of an additional band migrating at 65 kDa suggesting partial catabolism of the 72 kDa undigested recombinant polypeptide substrate had occurred in the presence of retinoic acid. This result indicates that the M1 epitope (at the N-terminal) was cleaved from the 72 kDa form of the IGD recombinant polypeptide substrate to generate a 65 kDa catabolite. The absence of positive immuunostaining for the 72 kDa band with anti M1 confirms this conclusion.

In order to ascertain if this cleavage of the IGD construct was occurring at the 'aggrecanase' site of the recombinant polypeptide substrate media samples of chondrocyte cultures treated with and without retinoic acid were examined by immunoblotting with monoclonal antibody BC-3 (anti ARGSV). Immunolocation with BC-3 showed no reactivity in cultures without retinoic acid and only one immunopositive band at 65 kDa in the retinoic acid treated cultures. This result indicates that "aggrecanase" catabolism of the 72 kDa form of the IGD recombinant polypeptide substrate has occurred in the presence of retinoic acid. However, there was no evidence that the 39 kDa isoform had been catabolized (as described in Example 3). Absence of immunostaining with BC-3 for positive 39 kDa form catabolites maybe due to these catabolites being present in lower concentrations since there was ten times more of the 72 kDa form in the rAGG-1 preparation than the 39 kDa form. In order to confirm that the 65 kDa catabolite was derived from the 72 kDa form of rAGG-1 the BC-3 immunoblot was reprobed with the anti M1 antibody. M1 immunodetected the uncleaved, parental peptide binds of 72 and 39 kD, and thus shows unequivocally that the BC-3 reactive cleavage product has a smaller molecular mass that the parental 72 kD band.

The results obtained with the recombinant IGD construct demonstrate that there is not a need for a G1 and/or a G2 domain on the IGD of aggrecan for cleavage at the 'aggrecanase' site. Reactivity with the aggrecanase-cleavage site-specific antibody BC-3 shows that the recombinant substrate rAGG-1 is cleaved at the aggrecanase site. Since this fusion protein does not contain a G1 or G2 domain, those domains are not essential for aggrecanase to be able to cleave rAGG-1 at the aggrecanase cleavage site. Furthermore, there appears to be no requirement for keratan sulphate chains within the IGD which may give rigidity to this region in the native aggrecan molecule, because the rAGG-1 construct showed no positive staining on Western blot analysis with an anti-keratan sulphate antibody 5-D-4.

Example 9
Analysis of Native Bovine A1D1 From Agarose Cultures Treated with and without Retinoic Acid The use of a native substrate in this culture system was also evaluated to compare it with recombinant polypeptide substrate. Native bovine aggrecan (A1D1) was mixed with agarose containing rat chondrocytes treated with and without retinoic acid. Agarose cell cultures, without added bovine A1D1, were also analyzed in order to assay for any contribution of endogenous proteoglycan (potential substrate) synthesized during the 96 hours of culture.

When media samples were immunolocated with monoclonal antibody 2-B-6 no staining was seen in media taken from agarose cultures containing cells only. This result shows that there was no significant contribution of newly synthesized endogenous substrate in the culture period.

Cultures containing exogeneously added bovine aggrecan substrate maintained with and without retinoic acid show the predictable array of protein cores, 'ladders', as previously described by several studies (Hughes C E, et al., supra (1995); Ilic M Z, et al. *Biochem. Internat.* 1990; 21:977–986).

In contrast, immunostaining, using antibody BC-3, for the 'aggrecanase'-generated aggrecan catabolite with the N-terminal sequence ARGSV . . . was the only fragment observed in the cultures that were subjected to retinoic acid treatment. As stated above, retinoic acid stimulates "aggrecanase" activity in this culture system. The relative molecular weight of this BC-3 positive aggrecan catabolite was ~160 kDa and is similar to that observed in other culture systems (Hughes C E, et al., 1995).

Media and extract samples from cultures with both the recombinant polypeptide substrate and the native bovine aggrecan were also probed with a newly developed antibody (BC-14) that recognizes the N-terminal neoepitope sequence $F^{342}FGVG$ . . . that is formed after Matrix metalloproteinase (MMP) cleavage of human aggrecan that is generated by proteolysis of aggrecan IGD with MMP's 1, 2, 3, 7, 8 or 9. Immunoblotting with BC-14 was negative in both culture systems. This result indicates that catabolism of the IGD at this site was not occurring, a finding consistent with that reported from other laboratories (Lark M W, et al., 1995).

Example 10
Synthesis and Proteolysis of Mutated rAGG-1 Substrate

For further studies, the recombinant polypeptide substrate rAGG-1mut was employed, a version of our fusion protein rAGG-1, in which an alternate splice donor site at the aminoterminal end of the IGD was mutated to prevent alternative splicing. The parent construct rAGG-1 of rAGG-1mut contains a FLAG epitope as aminoterminal tag, the IGD of the human aggrecan, and the constant region of a human IgG molecule as a carboxyterminal tag. The amino acid sequence of rAGG-1mut differs only in position 34 from the amino acid sequence of rAGG-1: rAGG-1mut contains a Ala 34, while rAGG-1 contains a Gly 34. The nucleotide sequence of the DNA encoding rAGG-1mut differs in three positions from the DNA encoding rAGG-1: 2448: A to C, 2450: G to C and 2451: T to A.

Upon transient transfection, rAGG-1mut was secreted by COS cells as a fusion protein into the culture supernatant and ran as a 72 kD band under reducing conditions and as a 140 kD band under non reducing conditions, probably reflecting a dimerisation due to the presence of an unpaired cysteine in the hinge region of the human immunoglobulin component at the C-terminal of the construct.

Upon stimulation with retinoic acid (RA), agarose embedded cells of the rat chondrosarcoma cell line RX produce aggrecanase. rAGG-1mut is catabolised at the aggrecanase site as has been described for rAGG-1, which is shown through the immunodetection with the monoclonal antibody BC-3. The size of 66 kD of this catabolic product is in agreement with the predicted loss of 5.8 kD after cleavage at the aggrecanase site, $A^{374}RGSV$.

Priority application, European Application No. 96100682.2, filed Jan. 18, 1996, including the specification, drawings, claims and abstract, is hereby incorporated by reference.

We claim:

1. An isolated DNA sequence encoding a substrate for aggrecanase, wherein said substrate contains, as the only amino acid sequence of aggrecan, the interglobular domain of human aggrecan.

2. A DNA sequence encoding a substrate according to claim 1, wherein said DNA sequence comprises the nucleotide sequence of nucleotides 2350 to 4114 of FIG. 7 (SEQ. ID NO. 4).

3. A DNA sequence encoding a substrate according to claim 1, wherein said DNA sequence comprises a portion of the nucleotide sequence of nucleotides 2350 to 4114 of FIG. 7 (SEQ. ID NO. 4).

4. A DNA sequence encoding a substrate according to claim 1, wherein said DNA sequence hybridizes under stringent conditions with the nucleotide sequence of nucleotides 2350 to 4114 of FIG. 7 (SEQ. ID NO. 4).

5. A vector comprising a DNA sequence as claimed in claim 1.

6. A host cell comprising a vector as claimed in claim 5.

7. A vector comprising the nucleotide sequence set forth in FIG. 7 (SEQ ID NO:4).

8. An isolated DNA sequence encoding a polypeptide substrate for aggrecanase as claimed in claim 1, wherein said substrate comprises a portion of the sequence as set forth in FIG. 6 (SEQ. ID NO. 3).

9. An isolated DNA sequence encoding a substrate for aggrecanase, wherein said substrate comprises the following components, beginning with the N-terminus and ending with the C-terminus:
   a) the signal sequence of CD5;
   b) the FLAG-epitope;
   c) the interglobular domain of human aggrecan;
   d) the hinge region of human IgG1;
   e) the CH2 region of human IgG1; and
   f) the CH3 region of human IgG1.

10. An isolated DNA sequence encoding a polypeptide substrate for aggrecanase, wherein said substrate comprises the amino acid sequence as set forth in FIG. 6 (SEQ. ID NO. 3).

11. An isolated DNA sequence encoding a polypeptide substrate for aggrecanase, wherein said substrate comprises the amino acid sequence as set forth in FIG. 6 (SEQ. ID NO. 3) and wherein amino acid 34 is mutated to Ala.

12. An isolated DNA sequence encoding a substrate as claimed in claim 11, wherein said substrate comprises a portion of the amino acid sequence as set forth in FIG. 6 (SEQ. ID NO. 3) and wherein amino acid 34 is mutated to Ala.

13. A cell culture system for monitoring aggrecanase activity in a sample comprising:
   (a) mixing freshly isolated chondrocyte cells and a substrate for aggrecanase encoded by the DNA of claim 1;
   (b) incubating the reaction mixture of step (a); and
   (c) detecting the presence or absence of aggrecanase activity in the reaction mixture,
   wherein aggrecanase activity is determined by the presence of aggrecanase peptide cleavage products.

14. A system as claimed in claim 13, wherein said system is free of endogenous proteoglycans or other extracellular components.

15. A system as claimed in claim 13, wherein the presence or absence of cleavage products is measured by determining the presence of peptide cleavage products that react with monoclonal antibodies specific for aggrecanase cleavage products.

16. A system as claimed in claim 15, wherein said monoclonal antibody detects a peptide having an amino acid sequence ARGSV.

17. A system as claimed in claim 13, wherein aggrecanase activity of said chondrocytes is stimulated by adding retinoic acid to the reaction mixture of step (a).

18. A method for cloning cDNA encoding aggrecanase, comprising:
   (a) preparing a cDNA expression library from cells expressing aggrecanase;
   (b) transfecting suitable cells with the library of step (a), wherein said cells express said cDNA in said expression library;
   (c) incubating the cells of step (b) with a substrate for aggrecanase encoded by the DNA of claim 1; and
   (d) detecting the presence of an aggrecanase cleavage product produced by a cell of step (c).

19. A method for screening for an aggrecanase inhibitor, comprising:
   (a) mixing freshly isolated chondrocyte cells and a substrate for aggrecanase encoded by the DNA of claim 1;
   (b) incubating the reaction mixture of step (a) in the presence or absence of a putative aggrecanase inhibitor; and
   (c) detecting the presence or absence of aggrecanase activity in the reaction mixture
   wherein aggrecanase activity is determined by the presence of aggrecanase peptide cleavage products.

20. A method for monitoring the onset of osteoarthritis, said method comprising assaying a sample of biological fluid from a patient for the presence of aggrecanase, wherein said aggrecanase activity is measured using a system as claimed in claim 12.

21. A method for monitoring the progression of osteoarthritis, said method comprising assaying a sample of biological fluid from a patient suffering from osteoarthritis for the presence of aggrecanase, wherein said aggrecanase activity is measured using a system as claimed in claim 13.

22. A method as claimed in claim 20, wherein said biological fluid is selected from the group consisting of synovial fluid, urine, serum, and lymph fluid.

23. A method as claimed in claim 21, wherein said biological fluid is selected from the group consisting of synovial fluid, urine, serum, and lymph fluid.

24. A method as claimed in claim 21, wherein said method is used to follow disease progression to determine the effectiveness of therapeutic treatment.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 58 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: exon
      (B) LOCATION: 1..58

(xi) SEQUENCE DESCRIPTION: SEQ ID NO: 1:

CGCGGGGCTA GCCGACTACA AGGACGACGA TGACAAGACA GGTGAAGACT TTGTGGAC  58

(2) INFORMATION FOR SEQ ID NO: 2:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..38

(xi) SEQUENCE DESCRIPTION: SEQ ID NO: 2:

CGCGGGGGAT CCCCTCCCCC TGGCAAATGC GGCTGCCC  38

(2) INFORMATION FOR SEQ ID NO: 3:

(i) SEQUENCE CHARACTERISTICS:
        (A) LENGTH: 396 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..396

(xi) SEQUENCE DESCRIPTION: SEQ ID NO: 3:

```
Met Pro Met Gly Ser Leu Gln Pro Leu Ala Thr Leu Tyr Leu Leu Gly
 1               5                  10                  15

Met Leu Val Ala Ser Val Leu Ala Asp Tyr Lys Asp Asp Asp Lys
                20                  25                  30

Thr Gly Glu Asp Phe Val Asp Ile Pro Glu Asn Phe Phe Gly Val Gly
                35                  40                  45

Gly Glu Glu Asp Ile Thr Val Gln Thr Val Thr Trp Pro Asp Met Glu
50                  55                  60

Leu Pro Leu Pro Arg Asn Ile Thr Glu Gly Glu Ala Arg Gly Ser Val
65                  70                  75                  80

Ile Leu Thr Val Lys Pro Ile Phe Glu Val Ser Pro Ser Pro Leu Glu
                85                  90                  95

Pro Glu Glu Pro Phe Thr Phe Ala Pro Glu Ile Gly Ala Thr Ala Phe
                100                 105                 110

Ala Glu Val Glu Asn Glu Thr Gly Glu Ala Thr Arg Pro Trp Gly Phe
                115                 120                 125

Pro Thr Pro Gly Leu Gly Pro Ala Thr Ala Phe Thr Ser Glu Asp Leu
                130                 135                 140

Val Val Gln Val Thr Ala Val Pro Gly Gln Pro His Leu Pro Gly Gly
145                 150                 155                 160

Gly Asp Pro Glu Glu Pro Lys Ser Cys Asp Lys Thr His Thr Cys Pro
                165                 170                 175

Pro Cys Pro Ala Pro Glu Leu Leu Gly Gly Pro Ser Val Phe Leu Phe
                180                 185                 190

Pro Pro Lys Pro Lys Asp Thr Leu Met Ile Ser Arg Thr Pro Glu Val
                195                 200                 205
```

```
Thr Cys Val Val Val Asp Val Ser His Glu Asp Pro Glu Val Lys Phe
    210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Arg Glu Pro Gln Val Tyr Thr Leu Pro Pro Ser Arg
    290                 295                 300

Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Lys Leu Thr Val Asp Lys Ser Arg Trp Gln Gln
        355                 360                 365

Gly Asn Val Phe Ser Cys Ser Val Met His Glu Ala Leu His Asn His
    370                 375                 380

Tyr Thr Gln Lys Ser Leu Ser Leu Ser Pro Gly Lys
385                 390                 395
```

(2) INFORMATION FOR SEQ ID NO: 4:

(i) SEQUENCE CHARACTERISTICS:
        (A) LENGTH: 5337 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..5337

(xi) SEQUENCE DESCRIPTION: SEQ ID NO: 4:

```
GGCGTAATCT GCTGCTTGCA AACAAAAAAA CCACCGCTAC CAGCGGTGGT TTGTTTGCCG      60
GATCAAGAGC TACCAACTCT TTTTCCGAAG GTAACTGGCT TCAGCAGAGC GCAGATACCA     120
AATACTGTCC TTCTAGTGTA GCCGTAGTTA GGCCACCACT TCAAGAACTC TGTAGCACCG     180
CCTACATACC TCGCTCTGCT AATCCTGTTA CCAGTGGCTG CTGCCAGTGG CGATAAGTCG     240
TGTCTTACCG GGTTGGACTC AAGACGATAG TTACCGGATA AGGCGCAGCG GTCGGGCTGA     300
ACGGGGGGTT CGTGCACACA GCCCAGCTTG GAGCGAACGA CCTACACCGA ACTGAGATAC     360
CTACAGCGTG AGCATTGAGA AAGCGCCACG CTTCCCGAAG GGAGAAAGGC GGACAGGTAT     420
CCGGTAAGCG GCAGGGTCGG AACAGGAGAG CGCACGAGGG AGCTTCCAGG GGGAAACGCC     480
TGGTATCTTT ATAGTCCTGT CGGGTTTCGC CACCTCTGAC TTGAGCGTCG ATTTTTGTGA     540
TGCTCGTCAG GGGGGCGGAG CCTATGGAAA AACGCCAGCA ACGCAAGCTA GCTTCTAGCT     600
AGAAATTGTA AACGTTAATA TTTTGTTAAA ATTCGCGTTA AATTTTTGTT AAATCAGCTC     660
ATTTTTTAAC CAATAGGCCG AAATCGGCAA ATCCCTTAT AAATCAAAAG AATAGCCCGA      720
GATAGGGTTG AGTGTTGTTC CAGTTTGGAA CAAGAGTCCA CTATTAAAGA ACGTGGACTC     780
```

```
CAACGTCAAA GGGCGAAAAA CCGTCTATCA GGGCGATGGC CGCCCACTAC GTGAACCATC   840

ACCCAAATCA AGTTTTTTGG GGTCGAGGTG CCGTAAAGCA CTAAATCGGA ACCCTAAAGG   900

GAGCCCCCGA TTTAGAGCTT GACGGGGAAA GCCGGCGAAC GTGGCGAGAA AGGAAGGGAA   960

GAAAGCGAAA GGAGCGGGCG CTAGGGCGCT GGCAAGTGTA GCGGTCACGC TGCGCGTAAC  1020

CACCACACCC GCCGCGCTTA ATGCGCCGCT ACAGGGCGCG TACTATGGTT GCTTTGACGA  1080

GCACGTATAA CGTGCTTTCC TCGTTGGAAT CAGAGCGGGA GCTAAACAGG AGGCCGATTA  1140

AAGGGATTTT AGACAGGAAC GGTACGCCAG CTGGACCGCG GTCTTTCTCA ACGTAACACT  1200

TTACAGCGGC GCGTCATTTG ATATGATGCG CCCCGCTTCC CGATAAGGGA GCAGGCCAGT  1260

AAAAGCATTA CCCGTGGTGG GGTTCCCGAG CGGCCAAAGG GAGCAGACTC TAAATCTGCC  1320

GTCATCGACT TCGAAGGTTC GAATCCTTCC CCCACCACCA TCACTTTCAA AAGTCCGAAA  1380

GCTGCTCCCT GCTTGTGTGT TGGAGGTCGC TGAGTAGTGC GCGAGTAAAA TTTAAGCTAC  1440

AACAAGGCAA GGCTTGACCG ACAATTGCAT GAAGAATCTG CTTAGGGTTA GGCGTTTTGC  1500

GCTGCTTCGC GATGTACGGG CCAGATATAC GCGTTGACAT TGATTATTGA CTAGTTATTA  1560

ATAGTAATCA ATTACGGGGT CATTAGTTCA TAGCCCATAT ATGGAGTTCC GCGTTACATA  1620

ACTTACGGTA AATGGCCCGC CTGGCTGACC GCCCAACGAC CCCCGCCCAT TGACGTCAAT  1680

AATGACGTAT GTTCCCATAG TAACGCCAAT AGGGACTTTC CATTGACGTC AATGGGTGGA  1740

CTATTTACGG TAAACTGCCC ACTTGGCAGT ACATCAAGTG TATCATATGC CAAGTACGCC  1800

CCCTATTGAC GTCAATGACG GTAAATGGCC CGCCTGGCAT TATGCCCAGT ACATGACCTT  1860

ATGGGACTTT CCTACTTGGC AGTACATCTA CGTATTAGTC ATCGCTATTA CCATGGTGAT  1920

GCGGTTTTGG CAGTACATCA ATGGGCGTGG ATAGCGGTTT GACTCACGGG GATTTCCAAG  1980

TCTCCACCCC ATTGACGTCA ATGGGAGTTT GTTTTGGCAC CAAAATCAAC GGGACTTTCC  2040

AAAATGTCGT AACAACTCCG CCCCATTGAC GCAAATGGGC GGAATTCCTG GCGGGACTG  2100

GGGAGTGGCG AGCCCTCAGA TGCTGCATAT AAGCAGCTGC TTTTTGCCTG TACTGGGTCT  2160

CTCTGGTTAG ACCAGATCTG AGCCTGGGAG CTCTCTGGCT AACTAGAGAA CCCACTGCTT  2220

AAGCCTCAAT AAAGCTTCTA GAGATCCCTC GACCTCGAGA TCCATTGTGC TCTAAAGGAG  2280

ATACCCGGCC AGACACCCTC ACCTGCGGTG CCCAGCTGCC CAGGCTGAGG CAAGAGAAGG  2340

CCAGAAACCA TGCCCATGGG GTCTCTGCAA CCGCTGGCCA CCTTGTACCT GCTGGGGATG  2400

CTGGTCGCTT CCGTGCTAGC CGACTACAAG GACGACGATG ACAAGACAGG TGAAGACTTT  2460

GTGGACATCC CAGAAAACTT CTTTGGAGTG GGGGGTGAGG AGGACATCAC CGTCCAGACA  2520

GTGACCTGGC CTGACATGGA GCTGCCACTG CCTCGAAACA TCACTGAGGG TGAAGCCCGA  2580

GGCAGCGTGA TCCTTACCGT AAAGCCCATC TTCGAGGTCT CCCCCAGTCC CCTGGAACCC  2640

GAGGAGCCCT TCACGTTTGC CCCTGAAATA GGGGCCACTG CCTTCGCTGA GGTTGAGAAT  2700

GAGACTGGAG AGGCCACCAG GCCCTGGGC TTTCCCACAC CTGGCCTGGG CCCTGCCACG  2760

GCATTCACCA GTGAGGACCT CGTCGTGCAG GTGACCGCTG TCCCTGGGCA GCCGCATTTG  2820

CCAGGGGGAG GGGATCCCGA GGGTGAGTAC TAAGCTTCAG CGCTCCTGCC TGGACGCATC  2880

CCGGCTATGC AGCCCCAGTC CAGGGCAGCA AGGCAGGCCC CGTCTGCCTC TTCACCCGGA  2940

GGCCTCTGCC CGCCCCACTC ATGCTCAGGG AGAGGGTCTT CTGGCTTTTT CCCCAGGCTC  3000

TGGGCAGGCA CAGGCTAGGT GCCCCTAACC CAGGCCCTGC ACACAAAGGG GCAGGTGCTG  3060

GGCTCAGACC TGCCAAGAGC CATATCCGGG AGGACCCTGC CCTGACCTA AGCCCACCCC  3120

AAAGGCCAAA CTCTCCACTC CCTCAGCTCG GACACCTTCT CTCCTCCCAG ATTCCAGTAA  3180
```

```
CTCCCAATCT TCTCTCTGCA GAGCCCAAAT CTTGTGACAA AACTCACACA TGCCCACCGT    3240

GCCCAGGTAA GCCAGCCCAG GCCTCGCCCT CCAGCTCAAG GCGGGACAGG TGCCCTAGAG    3300

TAGCCTGCAT CCAGGGACAG GCCCCAGCCG GGTGCTGACA CGTCCACCTC CATCTCTTCC    3360

TCAGCACCTG AACTCCTGGG GGGACCGTCA GTCTTCCTCT TCCCCCCAAA ACCCAAGGAC    3420

ACCCTCATGA TCTCCCGGAC CCCTGAGGTC ACATGCGTGG TGGTGGACGT GAGCCACGAA    3480

GACCCTGAGG TCAAGTTCAA CTGGTACGTG GACGGCGTGG AGGTGCATAA TGCCAAGACA    3540

AAGCCGCGGG AGGAGCAGTA CAACAGCACG TACCGTGTGG TCAGCGTCCT CACCGTCCTG    3600

CACCAGGACT GGCTGAATGG CAAGGAGTAC AAGTGCAAGG TCTCCAACAA AGCCCTCCCA    3660

GCCCCCATCG AGAAAACCAT CTCCAAAGCC AAAGGTGGGA CCCGTGGGGT GCGAGGGCCA    3720

CATGGACAGA GGCCGGCTCG GCCCACCCTC TGCCCTGAGA GTGACCGCTG TACCAACCTC    3780

TGTCCCTACA GGGCAGCCCC GAGAACCACA GGTGTACACC CTGCCCCCAT CCGGGATGA    3840

GCTGACCAAG AACCAGGTCA GCCTGACCTG CCTGGTCAAA GGCTTCTATC CAGCGACAT    3900

CGCCGTGGAG TGGGAGAGCA ATGGGCAGCC GGAGAACAAC TACAAGACCA CGCCTCCCGT    3960

GCTGGACTCC GACGGCTCCT TCTTCCTCTA CAGCAAGCTC ACCGTGGACA AGAGCAGGTG    4020

GCAGCAGGGG AACGTCTTCT CATGCTCCGT GATGCATGAG GCTCTGCACA ACCACTACAC    4080

GCAGAAGAGC CTCTCCCTGT CTCCGGGTAA ATGAGTGCGA CGGCCGCGAC TCTAGAGGAT    4140

CTTTGTGAAG GAACCTTACT TCTGTGGTGT GACATAATTG GACAAACTAC CTACAGAGAT    4200

TTAAAGCTCT AAGGTAAATA TAAAATTTTT AAGTGTATAA TGTGTTAAAC TACTGATTCT    4260

AATTGTTTGT GTATTTTAGA TTCCAACCTA TGGAACTGAT GAATGGGAGC AGTGGTGGAA    4320

TGCCTTTAAT GAGGAAAACC TGTTTTGCTC AGAAGAAATG CCATCTAGTG ATGATGAGGC    4380

TACTGCTGAC TCTCAACATT CTACTCCTCC AAAAAAGAAG AGAAAGGTAG AAGACCCCAA    4440

GGACTTTCCT TCAGAATTGC TAAGTTTTTT GAGTCATGCT GTGTTTAGTA ATAGAACTCT    4500

TGCTTGCTTT GCTATTTACA CCACAAAGGA AAAAGCTGCA CTGCTATACA AGAAAATTAT    4560

GGAAAAATAT TCTGTAACCT TTATAAGTAG GCATAACAGT TATAATCATA ACATACTGTT    4620

TTTTCTTACT CCACACAGGC ATAGAGTGTC TGCTATTAAT AACTATGCTC AAAAATTGTG    4680

TACCTTTAGC TTTTTAATTT GTAAAGGGGT TAATAAGGAA TATTTGATGT ATAGTGCCTT    4740

GACTAGAGAT CATAATCAGC CATACCACAT TTGTAGAGGT TTTACTTGCT TTAAAAAACC    4800

TCCCACACCT CCCCCTGAAC CTGAAACATA AAATGAATGC AATTGTTGTT GTTAACTTGT    4860

TTATTGCAGC TTATAATGGT TACAAATAAA GCAATAGCAT CACAAATTTC ACAAATAAAG    4920

CATTTTTTTC ACTGCATTCT AGTTGTGGTT TGTCCAAACT CATCAATGTA TCTTATCATG    4980

TCTGGATCCT GTGGAATGTG TGTCAGTTAG GGTGTGGAAA GTCCCCAGGC TCCCCAGCAG    5040

GCAGAAGTAT GCAAAGCATG CATCTCAATT AGTCAGCAAC CAGGTGTGGA AAGTCCCCAG    5100

GCTCCCCAGC AGGCAGAAGT ATGCAAAGCA TGCATCTCAA TTAGTCAGCA ACCATAGTCC    5160

CGCCCCTAAC TCCGCCCATC CCGCCCCTAA CTCCGCCCAG TTCCGCCCAT TCTCCGCCCC    5220

ATGGCTGACT AATTTTTTTT ATTTATGCAG AGGCCGAGGC CGCCTCGGCC TCTGAGCTAT    5280

TCCAGAAGTA GTGAGGAGGC TTTTTTGGAG GCCTAGGCTT TTGCAAAAAG CTAATTC      5337
```